(12) United States Patent
Toda

(10) Patent No.: US 7,218,040 B2
(45) Date of Patent: May 15, 2007

(54) HANDHELD DEVICE HAVING ULTRASONIC TRANSDUCER FOR AXIAL TRANSMISSION OF ACOUSTIC SIGNALS

(75) Inventor: Minoru Toda, Lawrenceville, NJ (US)

(73) Assignee: Measurement Specialties, Inc., Hampton, VA (US)

(*) Notice: Subject to any disclaimer, the term of this patent is extended or adjusted under 35 U.S.C. 154(b) by 0 days.

(21) Appl. No.: 10/625,482

(22) Filed: Jul. 22, 2003

(65) Prior Publication Data

US 2004/0169439 A1 Sep. 2, 2004

Related U.S. Application Data

(60) Provisional application No. 60/453,322, filed on Mar. 10, 2003, provisional application No. 60/397,579, filed on Jul. 22, 2002.

(51) Int. Cl.
*H01L 41/08* (2006.01)
(52) U.S. Cl. .................................. 310/369
(58) Field of Classification Search ............. 310/328, 310/334, 348, 369, 800
See application file for complete search history.

(56) References Cited

U.S. PATENT DOCUMENTS

| | | | |
|---|---|---|---|
| 3,781,781 A * | 12/1973 | Groves, Jr. ............... | 367/155 |
| 4,825,116 A | 4/1989 | Itoh et al. | |
| 5,526,023 A | 6/1996 | Sugimoto et al. | |
| 5,717,168 A | 2/1998 | DeBuisser et al. | |
| 5,750,941 A | 5/1998 | Ishikawa et al. | |
| 6,118,205 A | 9/2000 | Wood et al. | |
| 6,239,535 B1 * | 5/2001 | Toda et al. ............... | 310/334 |
| 6,292,177 B1 | 9/2001 | Holtzman et al. | |
| 6,300,580 B1 | 10/2001 | Shenholz et al. | |
| 6,321,428 B1 * | 11/2001 | Toda et al. ............... | 29/25.35 |
| 6,335,723 B1 | 1/2002 | Wood et al. | |
| 6,400,065 B1 * | 6/2002 | Toda et al. ............... | 310/334 |
| 6,411,014 B1 * | 6/2002 | Toda ......................... | 310/334 |
| 6,414,673 B1 | 7/2002 | Wood et al. | |
| 6,633,280 B1 | 10/2003 | Matsumoto et al. | |
| 6,809,462 B2 * | 10/2004 | Pelrine et al. ............ | 310/319 |

(Continued)

FOREIGN PATENT DOCUMENTS

JP 2-221728 * 9/1990

(Continued)

OTHER PUBLICATIONS

International Search Report from corresponding PCT/US03/22883 dated Mar. 25, 2004.

(Continued)

*Primary Examiner*—Thomas M. Dougherty
(74) *Attorney, Agent, or Firm*—Plevy, Howard & Darcy, PC

(57) ABSTRACT

A handheld stylus having an elongated housing, a writing and drawing implement disposed within the housing and including a tip extending through an opening at an end of the housing where ultrasonic waves radiate therefrom and are used for determining a position of the stylus; and at least one ultrasonic transducer disposed within the housing. The transducer may be a cylindrical piezoelectric transducer having a holder and a cylindrical piezoelectric film spanning between at least two spaced apart cylindrical surfaces of the holder, or a flat transducer having a diaphragm, and a piezoelectric material disposed on a surface of the diaphragm.

16 Claims, 34 Drawing Sheets

U.S. PATENT DOCUMENTS

2001/0012002 A1    8/2001  Tosaya
2002/0089262 A1*   7/2002  Topa et al. ............... 310/334
2002/0148088 A1*  10/2002  Toda et al. ............... 29/25.35

FOREIGN PATENT DOCUMENTS

| JP | 2001-142639 | 5/2001 |
|---|---|---|
| WO | WO 00/62268 | 10/2000 |
| WO | WO 01/55957 | 8/2001 |

OTHER PUBLICATIONS

European Search Report dated Sep. 19, 2006 for Corresponding European Patent Application Number 03-76-5907.

* cited by examiner

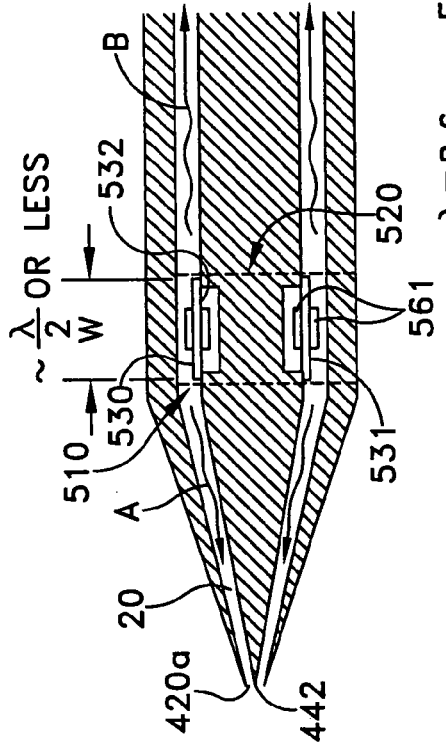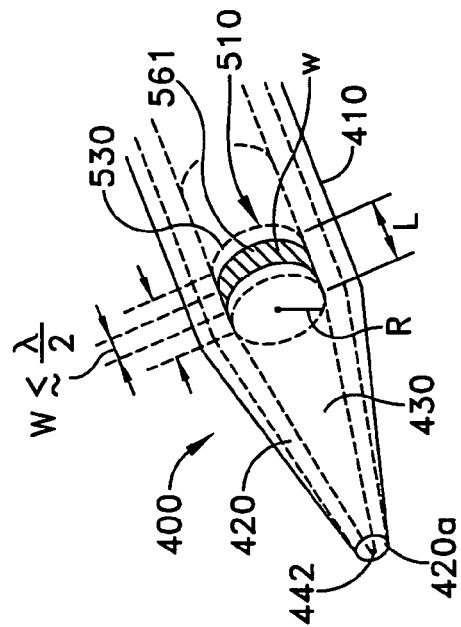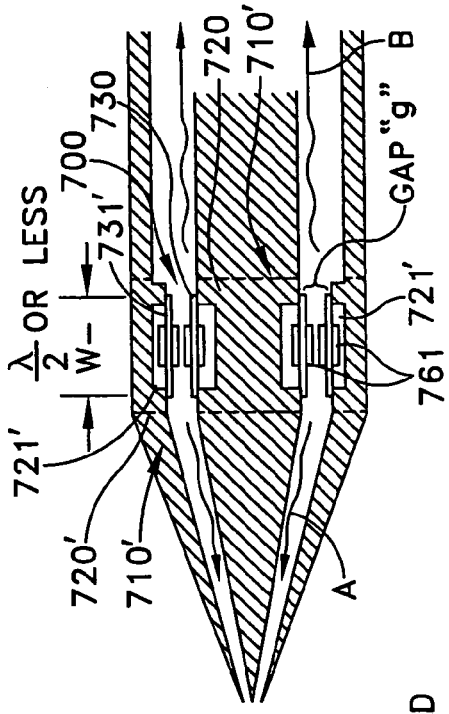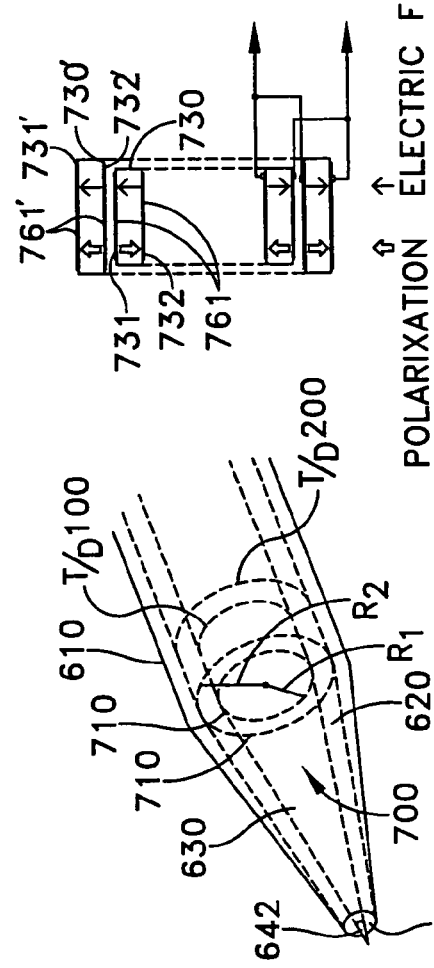

A-A'

B-B'

C-C'

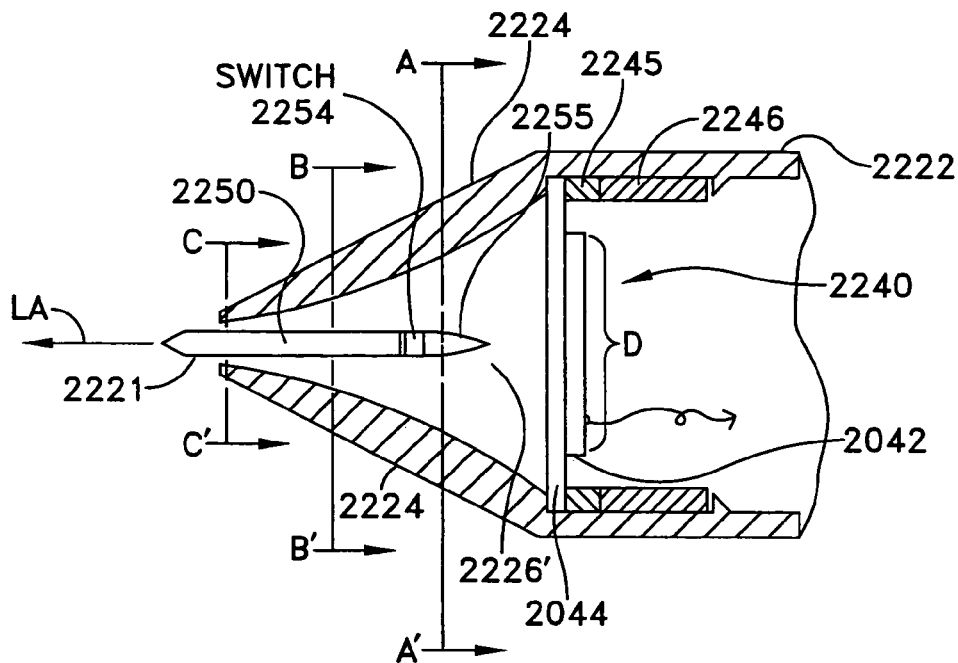
FIG. 26A
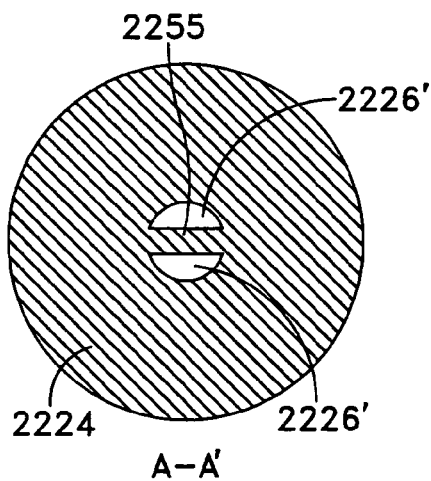
FIG. 26B
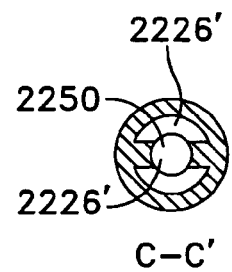
FIG. 26C
FIG. 26D

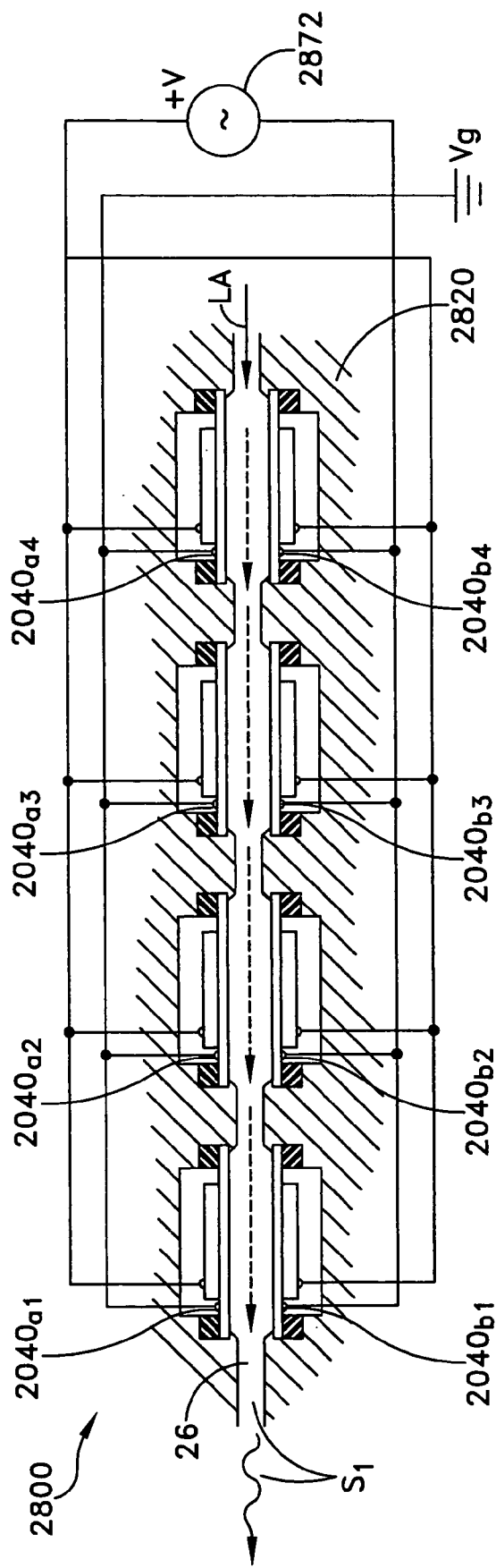
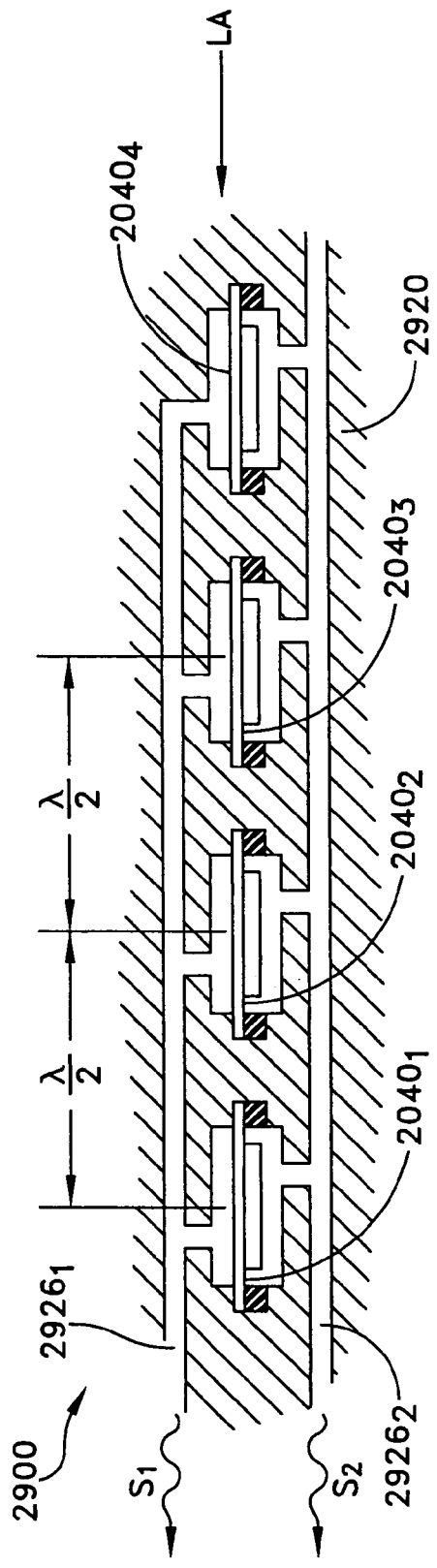
FIG. 32A
FIG. 32B

HANDHELD DEVICE HAVING ULTRASONIC TRANSDUCER FOR AXIAL TRANSMISSION OF ACOUSTIC SIGNALS

CLAIM FOR PRIORITY

This application claims the benefit under 35 U.S.C. 119(e) of U.S. Provisional Application Nos. 60/397,579, filed Jul. 22, 2002 and 60/453,322, filed Mar. 10, 2003.

FIELD OF THE INVENTION

The invention relates to ultrasonic transducers and more particularly to ultrasonic transducers used as transmitters and/or receivers in a handheld stylus device.

BACKGROUND OF THE INVENTION

Communications between an ultrasonic transducer mounted or positioned on a movable stylus (such as a movable pen) and other remotely located transducers (for example, transducers fixed at remote positions from the stylus) make it possible to determine the position of the pen and ultimately to reproduce information associated with stylus movement. The digital information associated with the stylus position might be used for drawings, maps, or pictorial illustrations, as well as for e-mail, sending of facsimiles, document creations, document and file creation reproduction (in combination with a word processor), or input devices for computer games, for example.

It is known that a piezoelectric film (e.g. PVDF film) wrapped around a cylindrical surface may be configured as an ultrasonic acoustic transducer. In the case where the transducer in U.S. Pat. No. 6,239,535 entitled "Omni-directional Ultrasound Transducer Apparatus" issued May 29, 2001 having a controlled frequency response operates as a transmitter, an acoustic wave is excited by an applied voltage and radiated in a radial direction. In the case of a receiver, radial waves incident onto the ultrasonic device are received and converted to voltage signals. The basic principle of operation of such transducers is that the film length in the molecular chain direction (i.e. machined direction) varies by applied voltage (or length variation by applied force induces voltage). The film in the machined direction is curved to form a cylinder so that the radius varies by an applied voltage to excite an acoustic wave. In the case of a receiver, an incoming acoustic pressure induces a change of radius and length in the arcuated direction to generate a voltage signal. Such a device is disclosed in commonly assigned U.S. Pat. No. 6,239,535 issued to Toda, et al. and incorporated herein by reference. In the case of a transmitter, an AC signal applied to the film electrodes causes a corresponding acoustic wave to be emitted from the transducer.

The main acoustic beam direction of the above mentioned device is perpendicular to the axis of the cylinder on which the piezoelectric film is wrapped. In the case of an ultrasonic pen or stylus, the cylindrical ultrasonic transducer is mounted or positioned on a movable stylus such as a movable pen and other remotely located transducers (for example, transducers fixed at remote positions from the stylus) receive signals emanating from the mounted transducer as the stylus moves, making it possible (via triangulation, for example) to determine the position of the pen and ultimately to reproduce information associated with stylus movement. The position of the cylindrical film should be slightly higher than the tip of the pen because the height of the cylinder is typically 3–5 millimeters (mm) for a 80 KHz design and doubles for a 40 KHz design. The ultrasonic wave radiates from the center of the cylinder and the center of radiation is several millimeters above the pen tip. When the position of the pen tip is fixed on a point of the writing surface and the angle of pen is varied, the effective position of the cylindrical transducer moves, and false information is transmitted because the system is designed to detect the absolute position of the transducer. Therefore, during writing or using of the pen, a person has to hold the pen at an exact, constant angle in order for the system to work as designed with maximum accuracy. Moreover, such transducers have been typically mounted externally on the pen, which causes additional problems for both the user, who must hold the stylus, and for the signal detection/transmission circuitry. Structures disposed about the outer surface of the stylus in a ring-like manner and placement of the structure at or substantially near the location of the stylus tip interfere with the user's ability to adequately grasp or hold the stylus. In addition, such location operates as an obstruction to the user's viewing of the information as it is being written. Accordingly, a need exists to provide an improved transducer apparatus mountable within a stylus for transmitting acoustic signals.

BRIEF DESCRIPTON OF THE DRAWINGS

FIG. 10A is a partial perspective view with broken lines depicting internal structures of another embodiment of a handheld stylus which utilizes another embodiment of a MSCUT according to the invention.

FIG. 10B is a sectional view of a portion of the stylus shown in FIG. 10A.

FIG. 11A is a partial perspective view with broken lines depicting internal structures of another embodiment of a handheld stylus which utilizes another embodiment of a MSCUT according to the invention.

FIG. 11B is a sectional view of a portion of the stylus shown in FIG. 11A.

FIG. 11C is a schematic view of the MSCUT show in FIGS. 11A and 11B.

Figure 22:
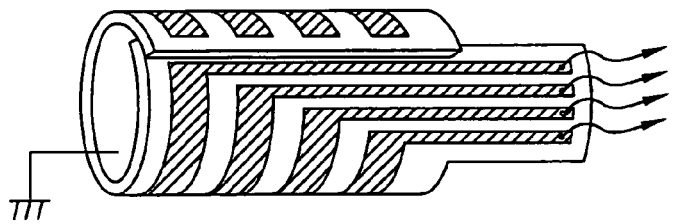
Figure 23:
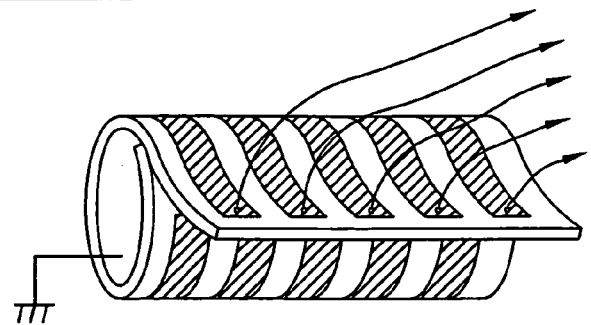

FIGS. 22 and 23 each show an embodiment of an electrode drive connection structure according to the invention, which may be used for connecting the ring electrodes to drive circuitry.

Figure 24A:
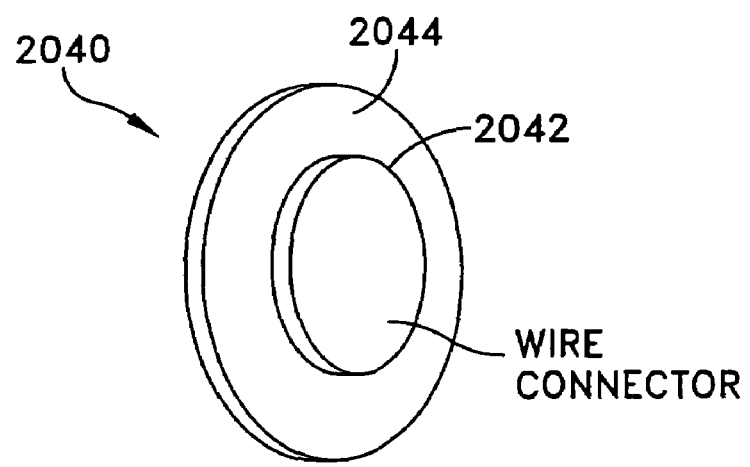

FIG. 24A is a perspective view of an embodiment of a flat ultrasonic transducer (FUT) according to the invention.

Figure 24B:
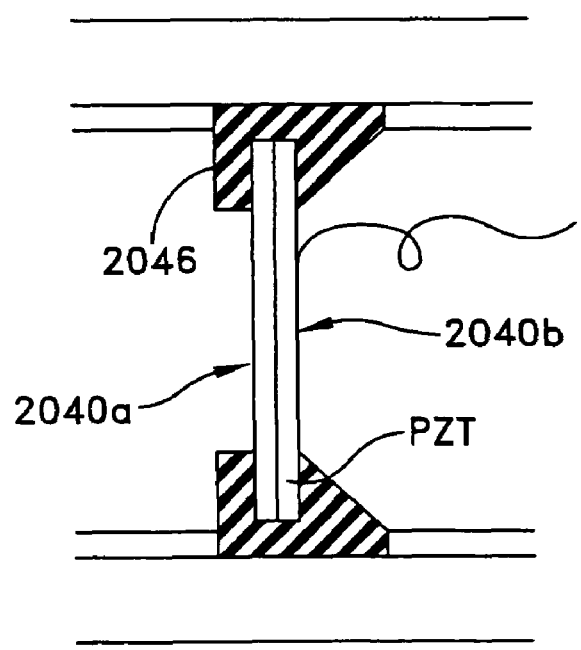

FIG. 24B is a side view of a FUT similar to the FUT shown in FIG. 24A, supported in a mounting member according to the invention.

Figure 25A:
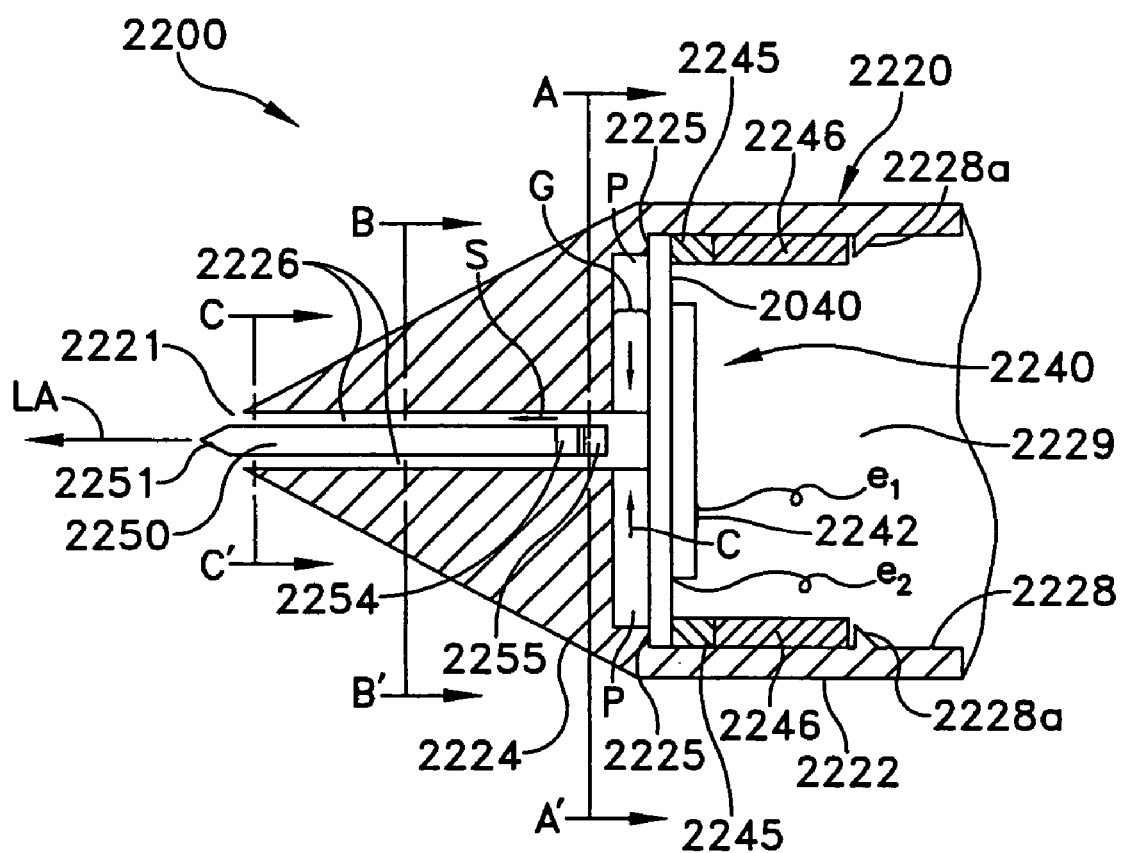

FIG. 25A is a sectional view of an embodiment of a handheld stylus according to the invention that utilizes the FUT of the invention.

Figure 25B:
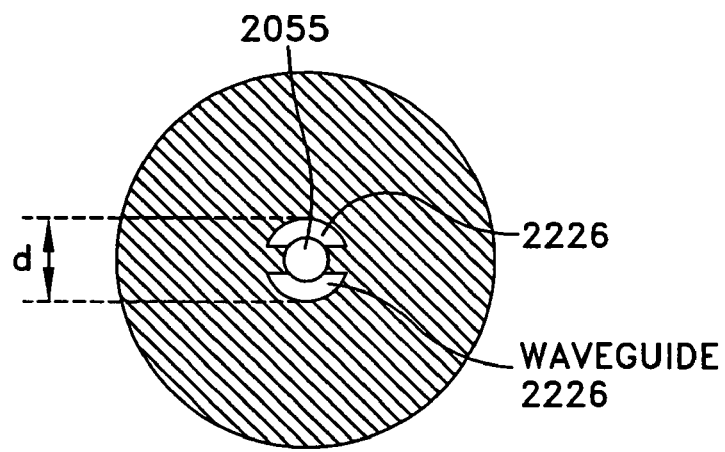

FIG. 25B is a sectional view through line A–A' of FIG. 25A.

Figure 25C:
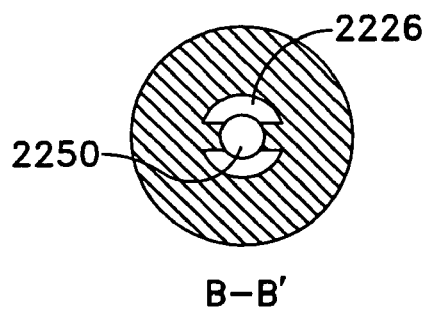

FIG. 25C is a sectional view through line B–B' of FIG. 25A.

Figure 25D:
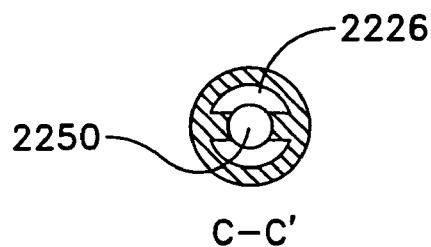

FIG. 25D is a sectional view through line C–C' of FIG. 25A.

FIG. 26A is a sectional view of another embodiment of a handheld stylus according to the invention that utilizes the FUT of the invention.

FIG. 26B is a sectional view through line A–A' of FIG. 26A.

FIG. 26C is a sectional view through line B–B' of FIG. 26A.

FIG. 26D is a sectional view through line C–C' of FIG. 26A.

Figure 27A:
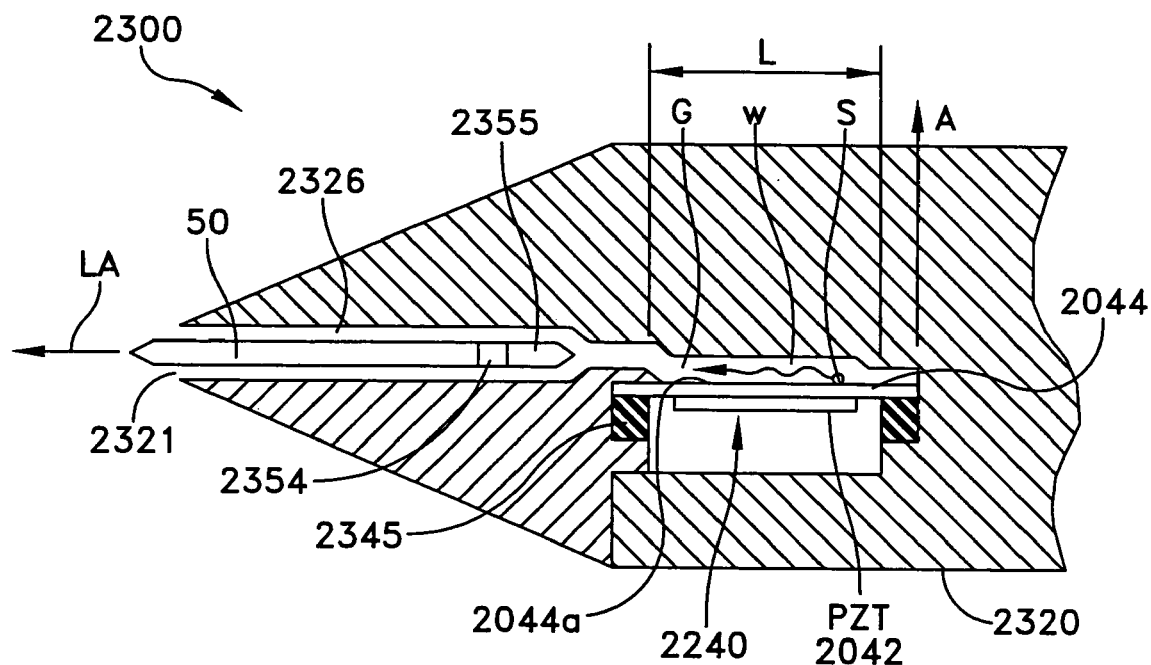

FIG. 27A is a sectional view of another embodiment of a handheld stylus according to the invention that utilizes the FUT of the invention.

Figure 27B:
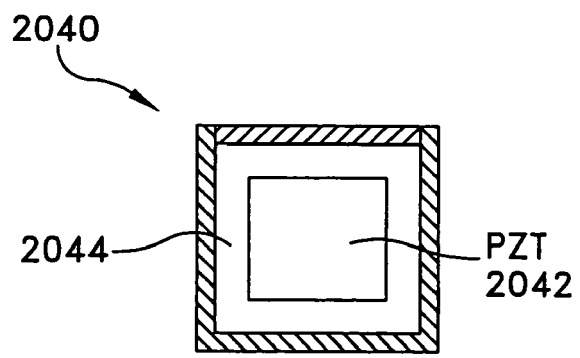

FIG. 27B is a plan view of the FUT used in the stylus shown in FIG. 27A.

Figure 28:
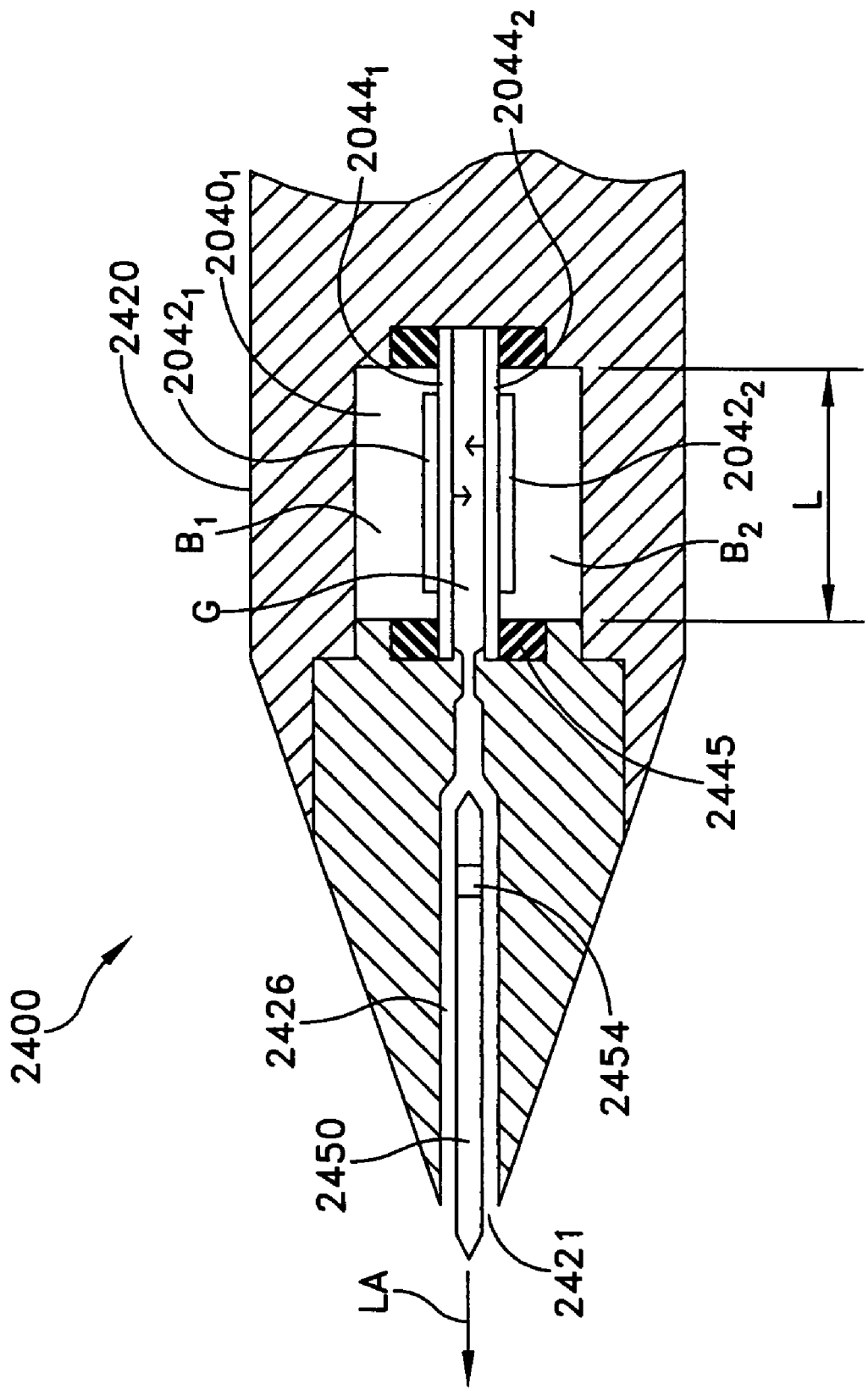

FIG. 28 is a sectional view of a further embodiment of a handheld stylus according to the invention that utilizes two FUTs of the invention.

Figure 29A:
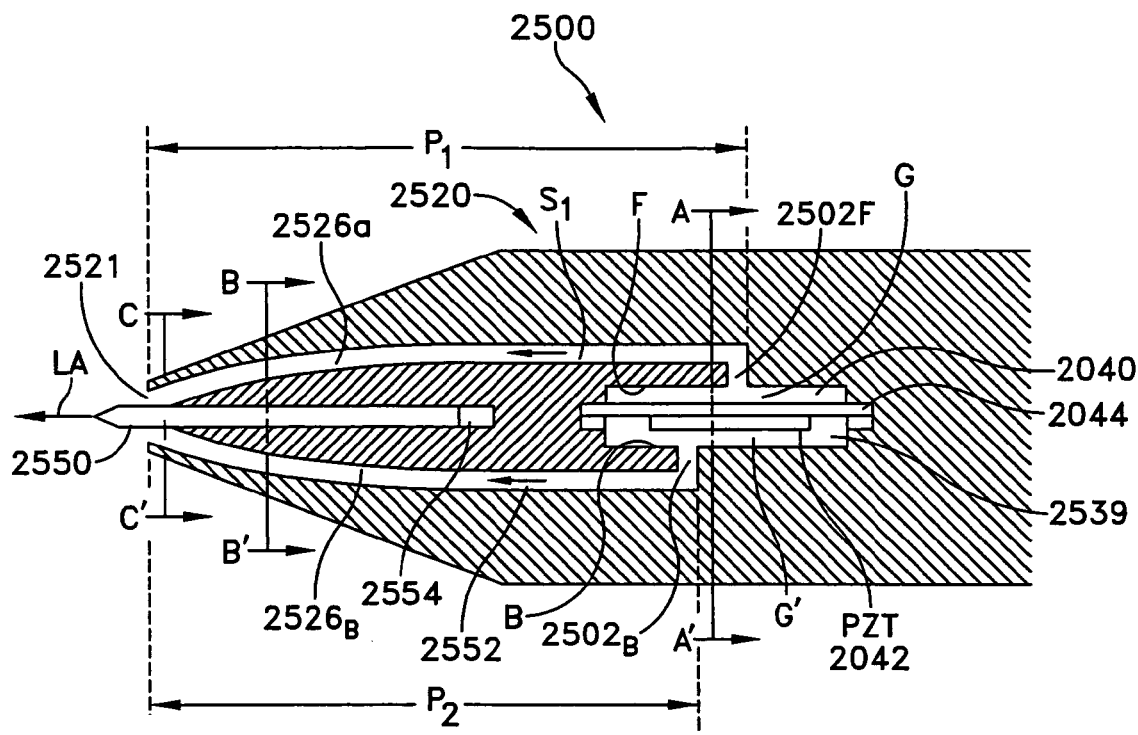

FIG. 29A is a sectional view of still another embodiment of a handheld stylus according to the invention that utilizes the FUT of the invention.

Figure 29B:
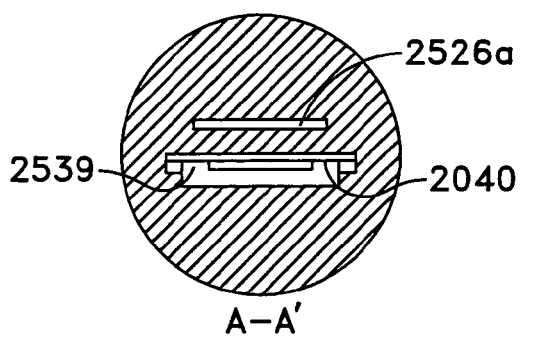

FIG. 29B is a sectional view through line A–A' of FIG. 29A.

Figure 29C:
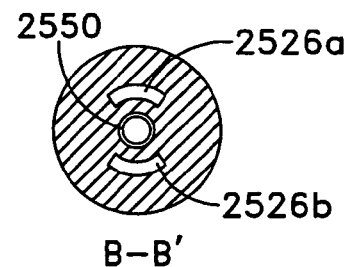

FIG. 29C is a sectional view through line B–B' of FIG. 29A.

Figure 29D:
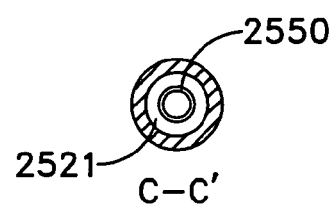

FIG. 29D is a sectional view through line C–C' of FIG. 29A.

Figure 30:
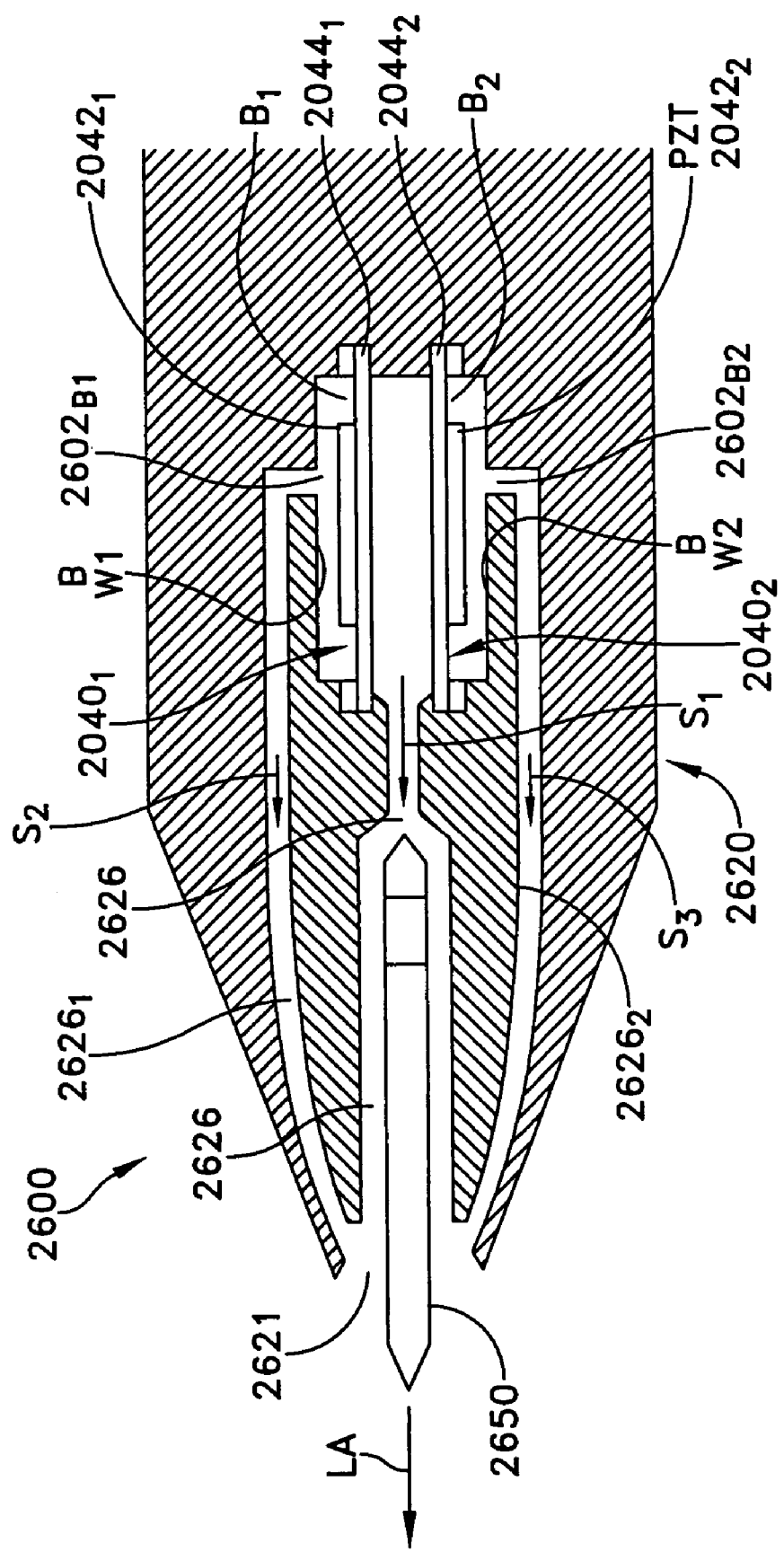

FIG. 30 is a sectional view of yet another embodiment of a handheld stylus according to the invention that utilizes two FUTs of the invention.

Figure 31A:
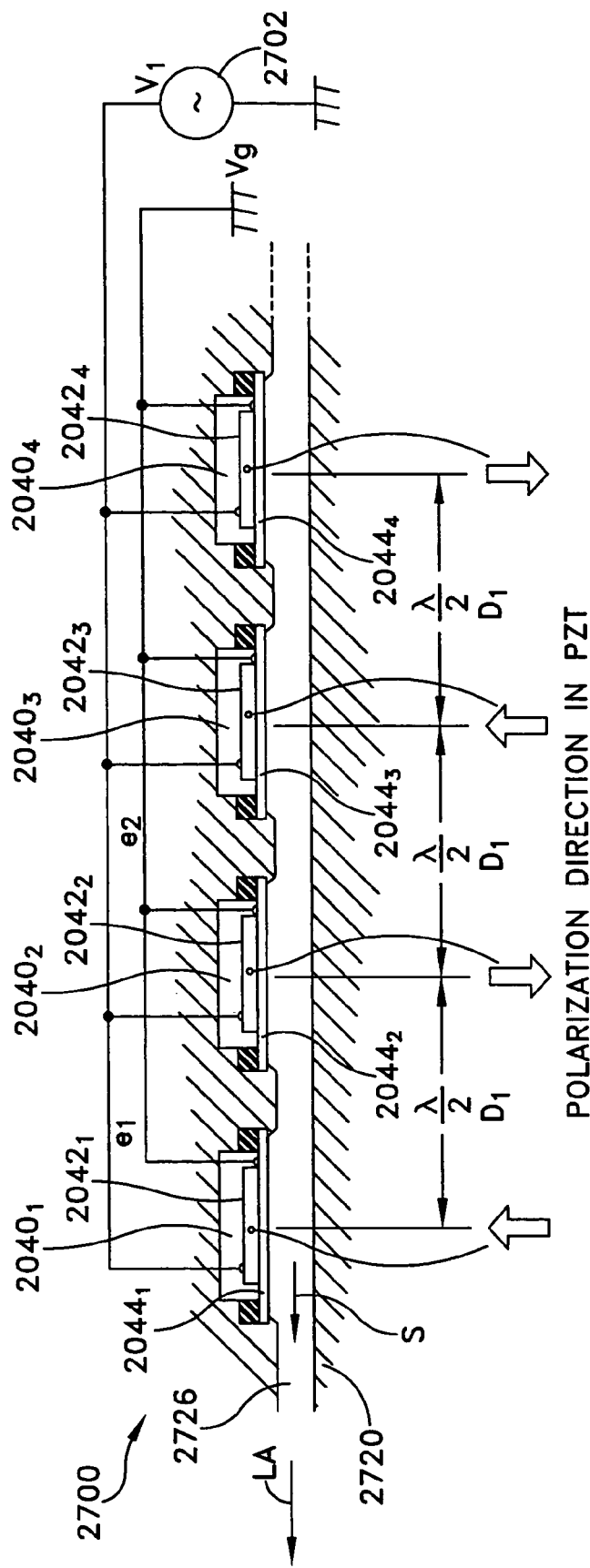

FIG. 31A is a sectional view of another embodiment of a handheld stylus according to the invention that utilizes multiple FUTs of the invention.

Figure 31B:
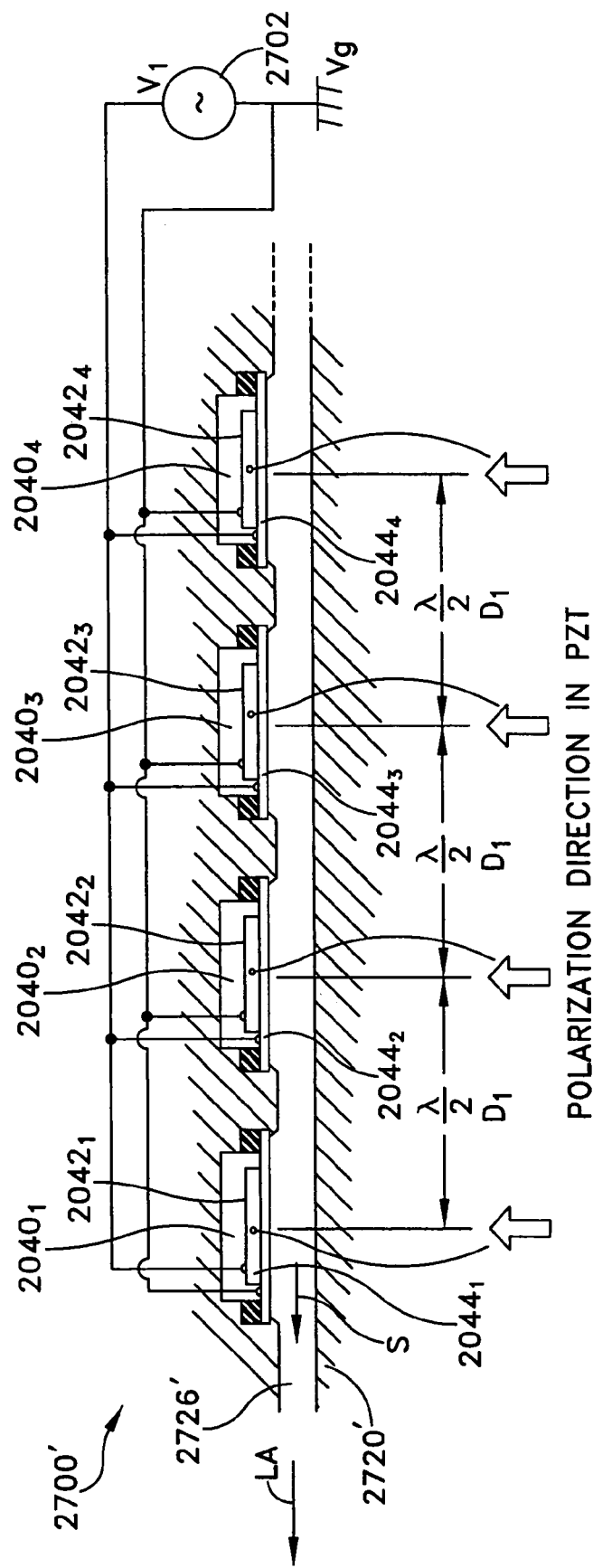

FIG. 31B is a sectional view of another embodiment of a handheld stylus according to the invention that utilizes multiple FUTs of the invention.

FIG. 32A is a sectional view of still another embodiment of a handheld stylus according to the invention that utilizes multiple FUTs of the invention.

FIG. 32B is a sectional view of yet another embodiment of a handheld stylus according to the invention that utilizes multiple FUTs of the invention.

Figure 33:
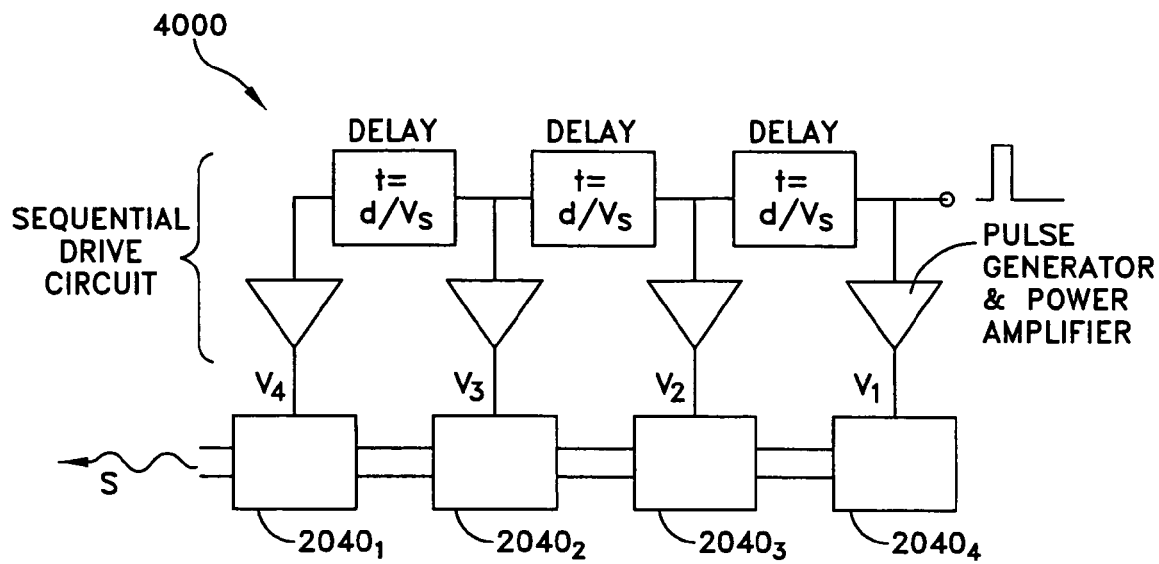

FIG. 33 shows an embodiment of a sequential drive circuit of the invention for driving multiple FUTs of the invention.

Figure 34:
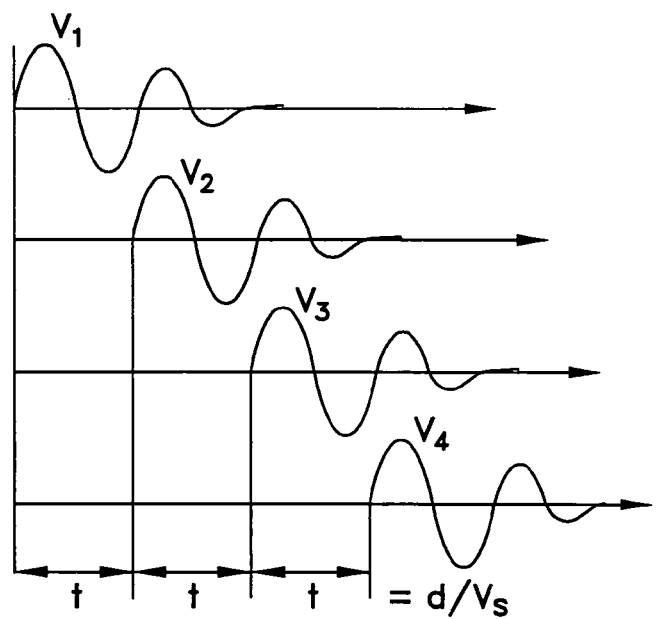

FIG. 34 is a graphical illustration of the excitation of each of the FUTs as a function of time by the sequential drive circuit shown in FIG. 33.

Figure 35:
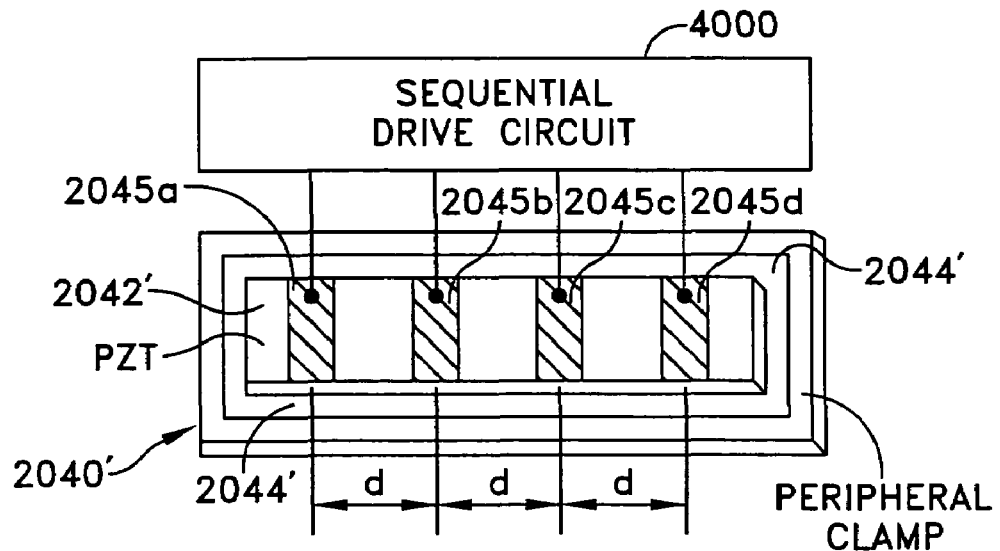

FIG. 35 illustrates another embodiment of a FUT according to the invention.

Figure 36:
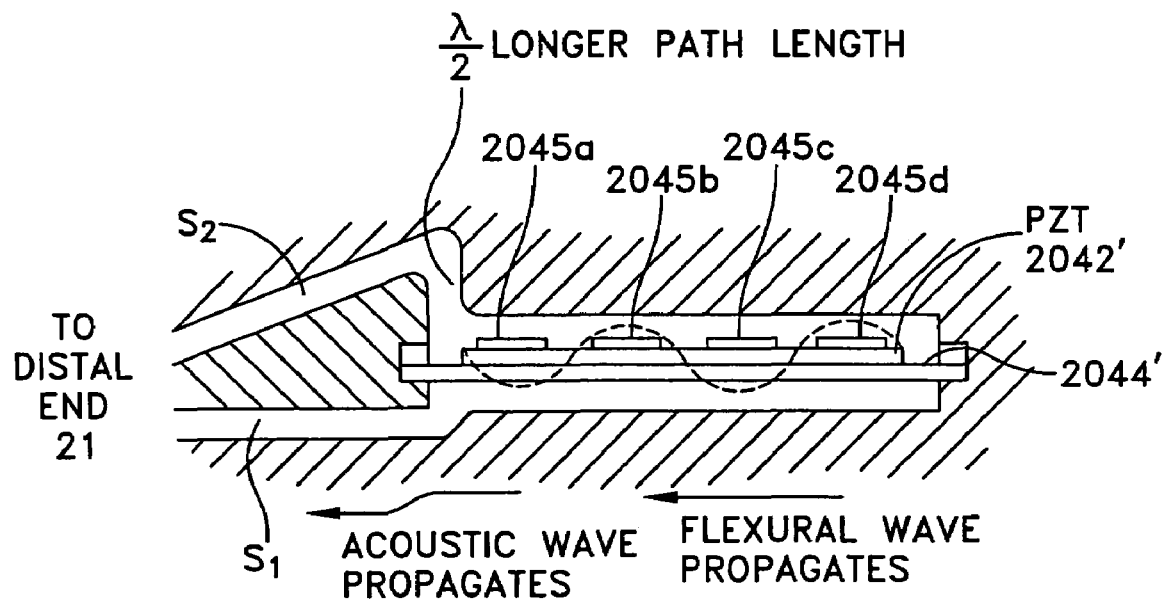

FIG. 36 is an exemplary illustration showing the acoustic propagation path associated with a sequentially driven multi electrode FUT shown in FIG. 35.

Figure 37:
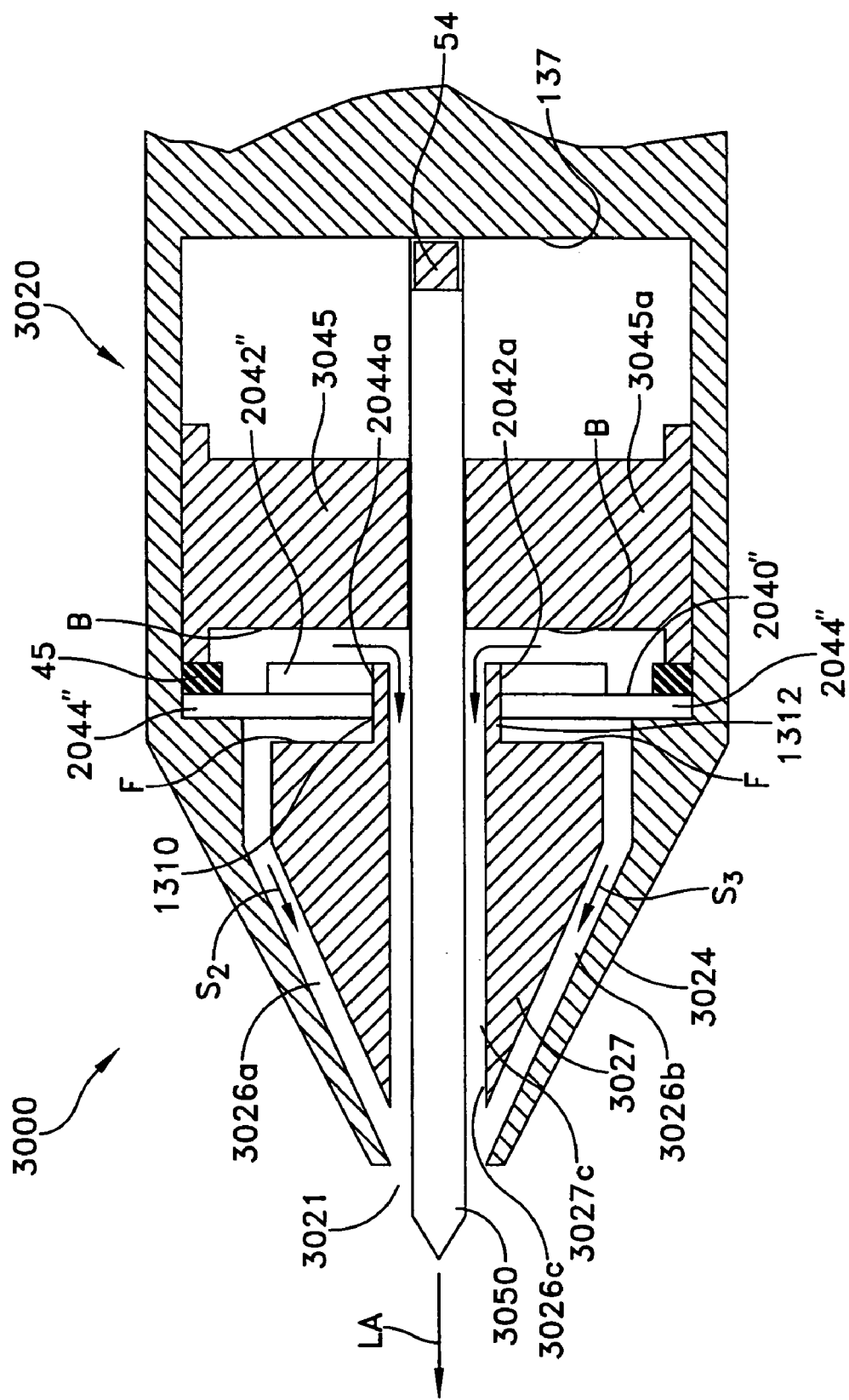

FIG. 37 is a sectional view of yet another embodiment of a handheld stylus according to the invention that utilizes another embodiment of a FUT of the invention.

Figure 38:
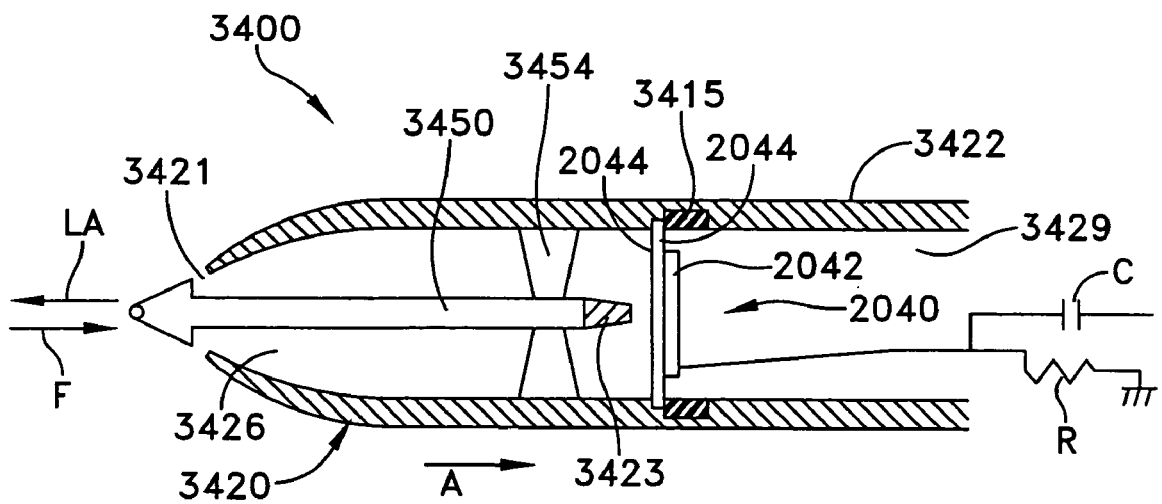

FIG. 38 is a sectional view of an embodiment of a handheld stylus according to the invention that utilizes the FUT of the invention for force detection.

Figure 39:
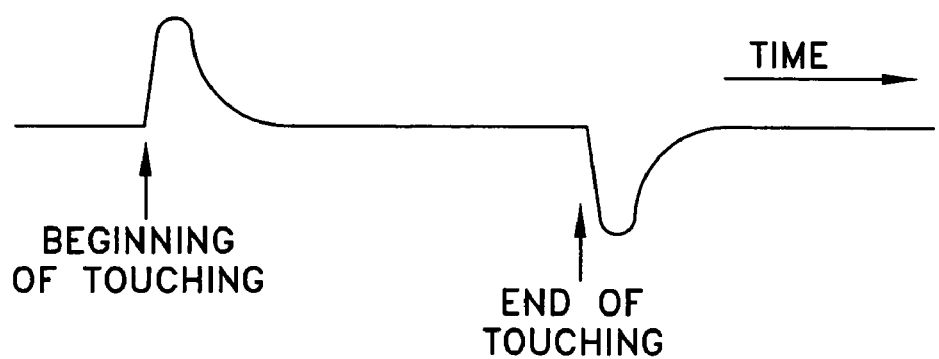

FIG. 39 is a graphical illustration showing a voltage signal generated by the piezoelectric transducer film of the stylus shown in FIG. 38 as it progresses from the beginning of a writing period to the end of the writing period.

Figure 40:
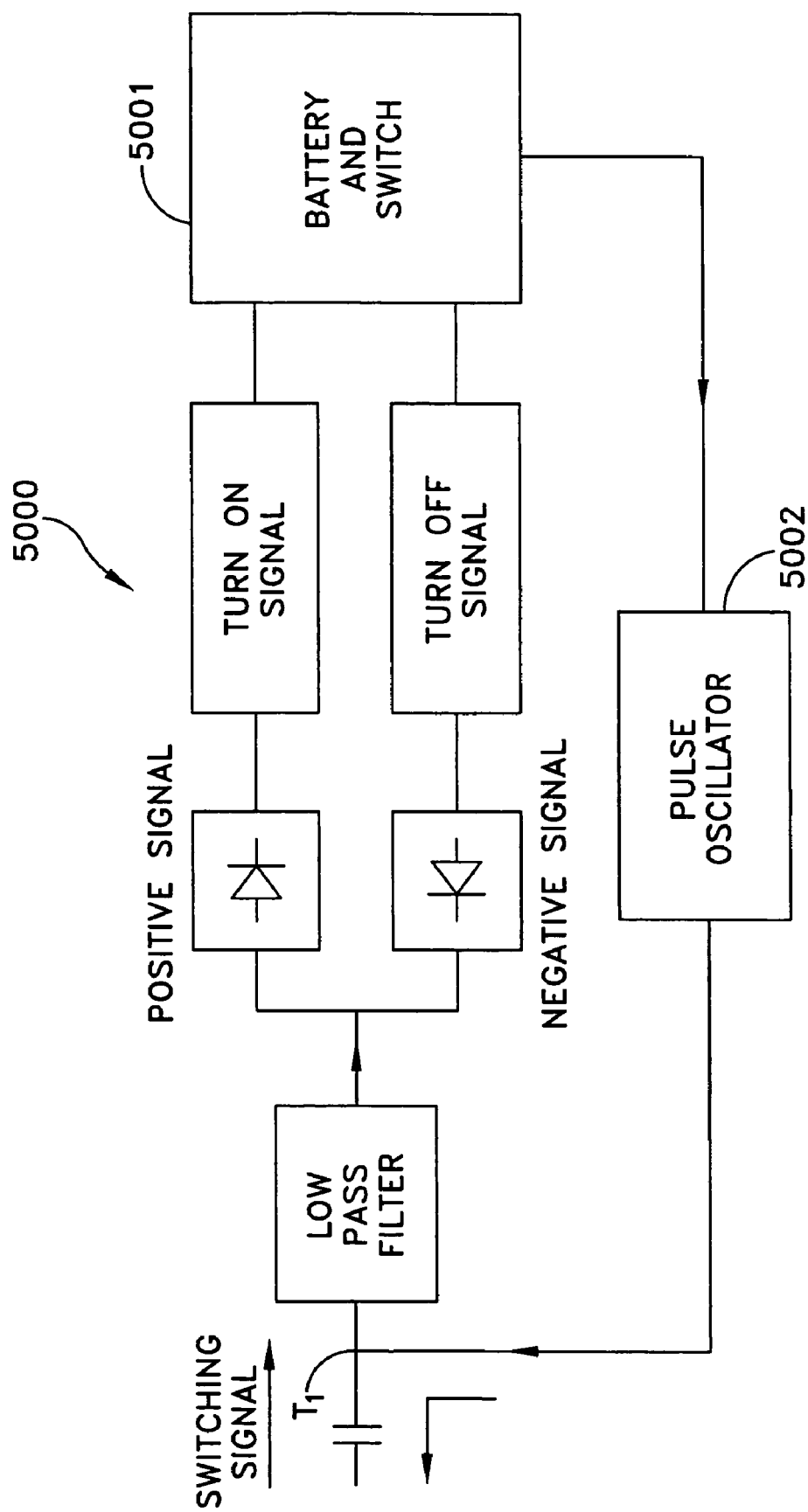

FIG. 40 shows an exemplary circuit for switching the FUT of the stylus shown in FIG. 38.

It is to be understood that these drawings are solely for purposes of illustrating the concepts of the invention and are not intended as a level of the limits of the invention. It will be appreciated that the same reference numerals, possibly supplemented with reference characters where appropriate, have been used throughout to identify corresponding parts.

DETAILED DESCRIPTION OF THE INVENTION

An aspect of the invention comprises a cylindrical ultrasonic transducer structure having axial acoustic transmission characteristics. The cylindrical ultrasonic transducer structure of the invention is especially intended for use as an ultrasonic transmitter. However, one of ordinary skill in the art will appreciate that the cylindrical ultrasonic transducer structure of the invention may also be utilized as a receiver.

Figure 1A:
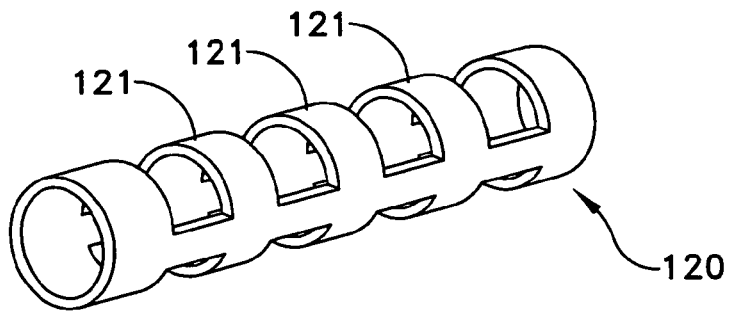
FIG. 1A is a perspective view of a mandrel or holder according to an embodiment of the invention.
Figure 1B:
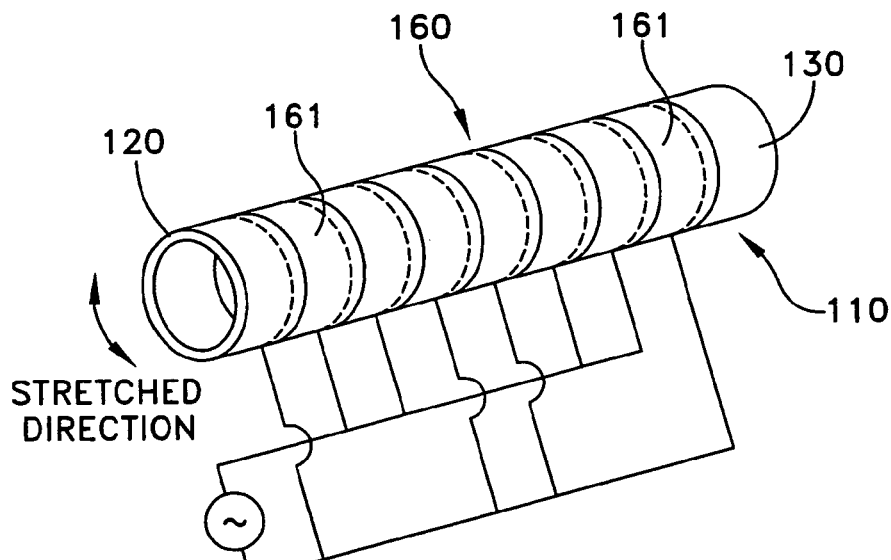
FIG. 1B is a perspective view of an embodiment of a multi-segment, cylindrical ultrasonic transducer (MSCUT) according to the invention which uses the holder shown in FIG. 1A.
Figure 1C:
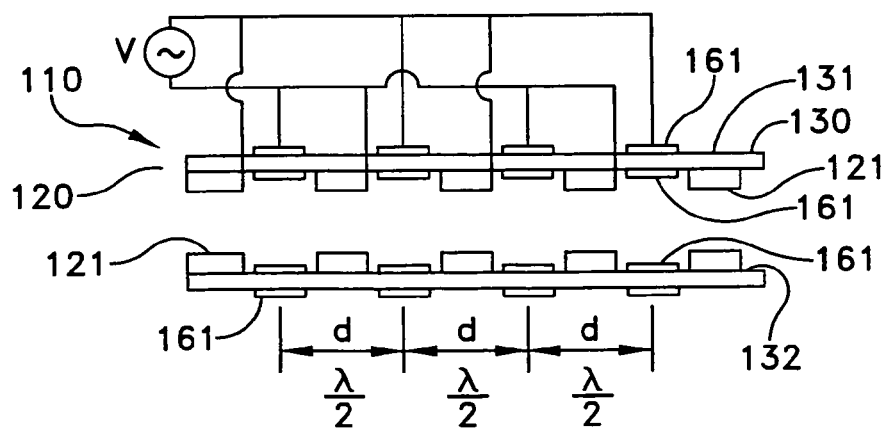
FIG. 1C is a sectional view of the MSCUT shown in FIG. 1B.
Figure 1D:
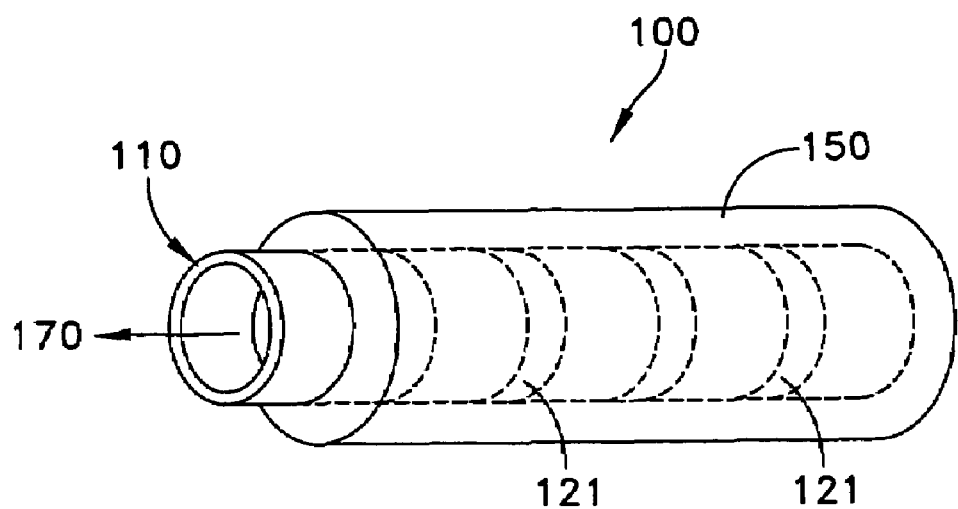
FIG. 1D is a perspective view of an embodiment of a MSCUT structure according to the invention which uses the MSCUT shown in FIGS. 1B and 1C.
Figure 1E:
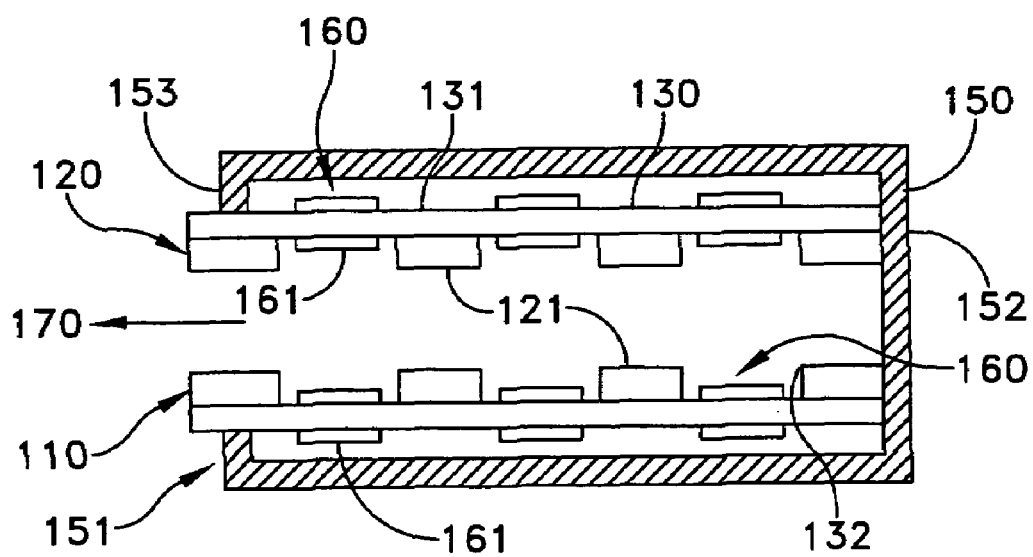
FIG. 1E is a sectional view of the MSCUT structure shown in FIG. 1D.
Figure 2A:
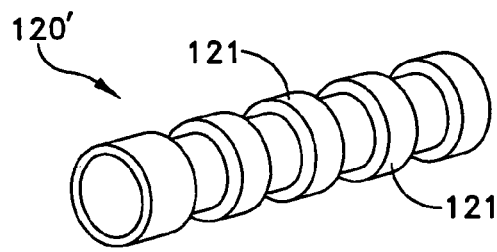
FIG. 2A is a perspective view of a mandrel or holder according to another embodiment of the invention.
Figure 2B:
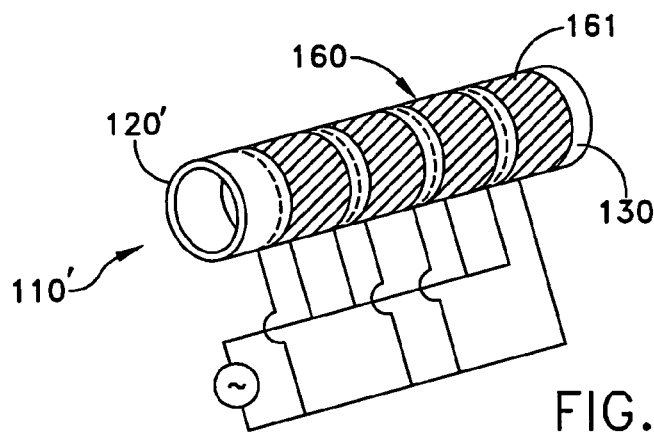
FIG. 2B is a perspective view of another embodiment of a MSCUT according to the invention which uses the holder shown in FIG. 2A.
Figure 2C:
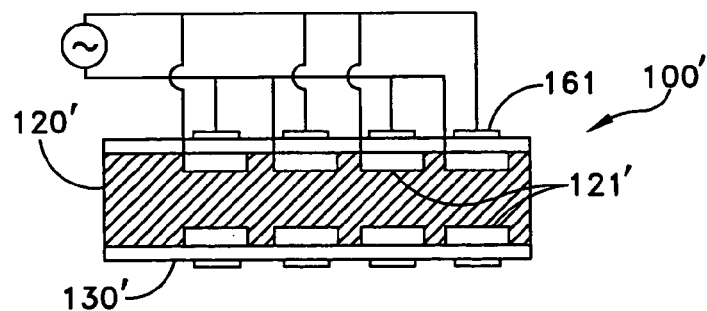
FIG. 2C is a sectional view of the MSCUT shown in FIG. 2B.
Figure 2D:
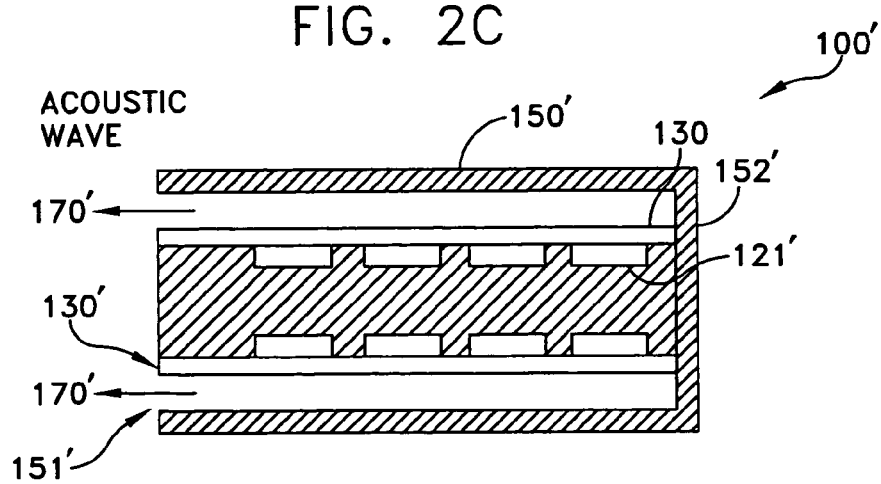
FIG. 2D is a sectional view of another embodiment of a MSCUT structure according to the invention which uses the MSCUT shown in FIGS. 2B and 2C.

Referring now to FIGS. 1A–1E, and initially to FIG. 1E, there is shown an embodiment of a multi-segment, cylindrical ultrasonic transducer (MSCUT) structure 100 according to the invention. The MSCUT structure 100 generally comprises a multi-segment, cylindrical transducer 110 disposed within a cylindrical cover 150 having an open first end 151 and a closed second end 152. The transducer 110 is formed by a generally hollow mandrel or holder 120 having multiple cylindrical sections 121 (FIG. 1A), and a cylindrical piezoelectric transducer film 130 disposed about the holder 120, for generating strong acoustic waves 170 in an axial direction of the transducer 110. The cylindrical piezoelectric transducer film 130 may be made from a piezoelectric material including, without limitation, polyvinylidene fluoride (PVDF), and may have a thickness of about 20–30 μm. A PVDF based film 130 is uniaxially stretched and poled during the processing and its molecular chains are aligned. The film 130 is formed into a cylinder with its stretched direction along curved or azimuthal direction.

As shown collectively in FIGS. 1A–1E, the piezoelectric film 130 includes a segmented electrode 160, defined by a plurality of electrode segments 161, disposed on outer and inner surfaces 131, 132 of the transducer film 130. The electrode segments 161 of the outer and inner segmented electrodes 160 are, preferably, uniformly sized and spaced apart from one another so as to cover corresponding sections 121 of the holder 120.

As shown in FIG. 1C, the center to center distance d between each pair of electrode segments 161 is about one-half wavelength of the acoustic wave in air, and an excitation voltage V is applied to the segments 161 on outer and interior surfaces 131, 132 of the transducer film 130 such that the phase of the excitation voltage alternates from one segment 161 to another. The voltage V applied to the piezoelectric transducer film 130 by means of electrode segments 161 causes acoustic waves to propagate along the outer and inner surfaces of the transducer 110. As shown in FIG. 1E, the cover 150 includes an inwardly directed flange 153 at the open end 151 thereof, which blocks and, therefore, inhibits the propagation path of the acoustic waves propagating along the outer surface of the transducer 110. In this manner, only the acoustic waves 170 propagating along the inner surface of the transducer 110 are emitted from the MSCUT structure 100.

FIGS. 2A–2D collectively illustrate another embodiment of a MSCUT structure according to the present invention, denoted by numeral 100'. In this embodiment, the multi-segment, cylindrical transducer 110' of the MSCUT structure 100' has a solid holder 120', which is constructed so that acoustic waves propagating along the inner surface of the transducer 110' are blocked (i.e., not used). Further, the cover 150' of the MSCUT structure 100' has an open end 151', which is constructed to allow acoustic waves 170' propagating along the outer surface of the transducer 110' to be emitted from the MSCUT structure 100'.

It should be understood, that the MSCUT structures 100, 100' depicted in FIGS. 1A–1E and 2A–2D may also be utilized as receivers, wherein an incident acoustic wave in the axial direction induces a voltage on the segmented electrodes 160. Since many electrode segments 161 are connected in parallel, the voltages generated thereby may be substantially the same and connected in parallel, the output current increases with increasing numbers N of electrode segments 161.

Figure 3:
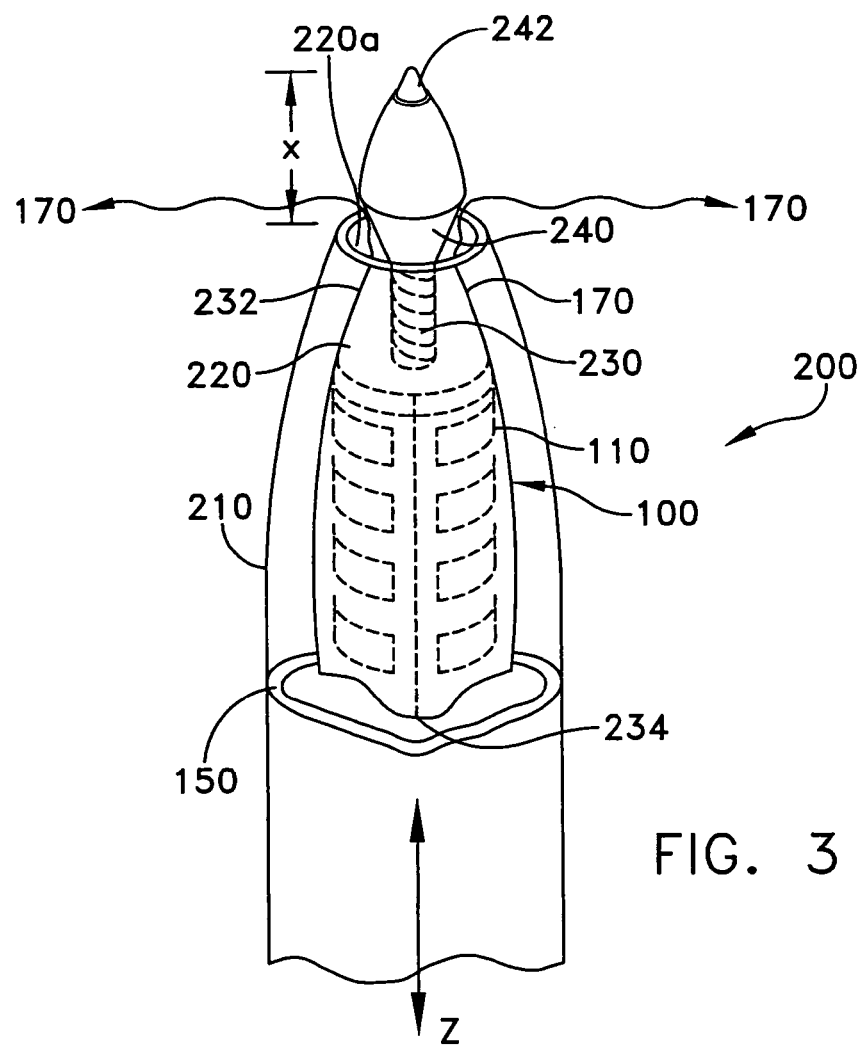
FIG. 3 is a partial side view with broken lines depicting internal structures of an embodiment of a handheld stylus which utilizes the MSCUT structure shown in FIGS. 1A–1E.

FIG. 3 illustrates an embodiment of a handheld stylus 200, which utilizes the MSCUT structure 110 of the invention. The stylus 200 comprises a housing 210 defining an internal bore 220 having opening 220a for receiving a writing and drawing implement 230 with a drawing and writing tip 242. The MSCUT structure 100 described earlier, is mounted within the internal bore 220 of the housing 210 and oriented along the longitudinal axis Z of the stylus for generating acoustic signals 170 along that axis Z. The closed second 152 (not visible in FIG. 3) of the cover 150 may be utilized to block any acoustic signal propagating in the direction opposite to that of opening 220a.

As previously mentioned, in ultrasonic pen or stylus applications, the acoustic wave beam or signal direction exiting the stylus must be generally perpendicular to the axis of stylus. The stylus position is calculated by the travel time of the acoustic wave beam or signal from the stylus to at least two fixed receivers. In order to convert the direction of a radiated acoustic wave to normal to the axis of the device, a reflector 240 may be provided at a neck 232 of the drawing implement 230 to redirect the acoustic wave beam or signal 170 exiting at the opening 220a to a substantially perpendicular direction relative to a drawing tip 242 of the implement 230. In a preferred embodiment, the reflector may be cone shaped. Note that the outer diameter of the reflector 240 may be smaller than the diameter of the the MSCUT. The distance x from opening 220a to the drawing tip 242 can be sized to be sufficiently small (e.g. 1 mm) such that the drawing tip location is substantially the location of the opening 220a, thereby minimizing tilt errors associated with the angle of the stylus 200 relative to the writing surface. Note that the conical reflector 240 does not operate effectively for a sufficiently small diameter (e.g. 2 mm–3 mm) single opening 220a, the radiating acoustic signal output from a such a small opening 220a diverges sufficiently, to about 90 degrees, enabling detection by a receiver positioned near (e.g. 5 mm–10 mm) to the writing surface. When the size of the reflector 240 becomes comparable or smaller than one-half of wavelength, the reflected wave spread and angle of reflection becomes insensitive to the direction of reflection. Accordingly no reflector is needed as will be described further on. Such a wave divergence from a small object is well know as diffraction.

An acoustic wave in the axial direction can be used for other applications including, without limitation, object presence detection by blocking between the transmitter and receiver, distance measurement, or pen positioning (i.e. wherein two ultrasonic transmitters are at fixed locations and a receiver transducer is mounted on a movable stylus). The beam divergence is controlled by the shape of the aperture.

Figure 4:
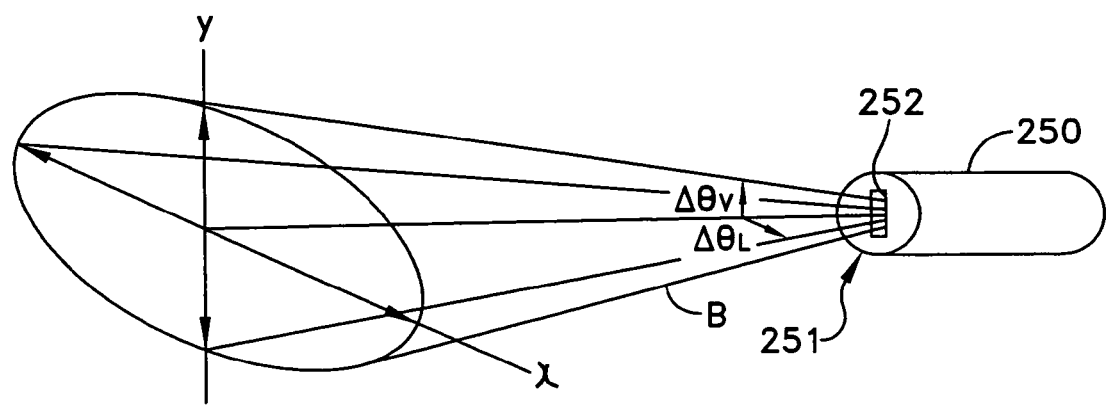
FIG. 4 is a schematic illustration of a diverging acoustic beam emanating from an output end of an acoustic transducer.

FIG. 4 is a schematic illustration of a diverging acoustic beam B emanating from an output end 251 of an acoustic transducer 250. Greater beam divergence $\Delta\theta v$ is manifested in the X direction than in the Y direction from a rectangular aperture 252 at the output end 251 of the transducer 250. This is because the vertical dimension of the aperture 252 is relatively large, such that beam divergence is less in the vertical direction while the horizontal dimension of the aperture 252 is relatively smaller, such that beam divergence $\Delta\theta v$ is larger in the horizontal direction. In the case of either a circular exit area with a small diameter or ring shaped exit area with the pen tip at the center, the small size of the exit area makes a circular beam profile with high divergence.

Figure 5A:
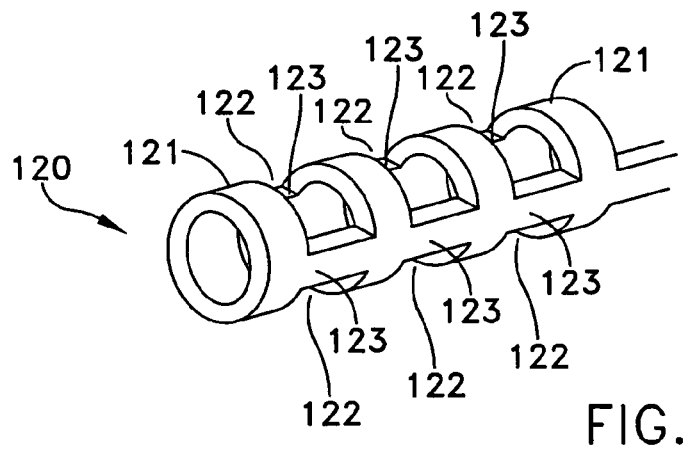
FIG. 5A is an enlarged perspective view of a portion of the mandrel or holder shown in FIG. 1A.

FIG. 5A is an enlarged view of the mandrel or holder 120 shown in FIG. 1A. As can be seen, the holder 120 comprises a cylindrical shape member having a plurality of axially separated, opposing cut-outs 122. The axially separated, opposing cut-outs 122 define the uniformly sized cylindrical sections 121 of the holder 120 and parallel connecting members 123, which axially connect the sections 121 to one another. The cylindrical sections 121 and the connecting members 123 define a cylindrical outer surface that accommodates the piezoelectric film 130 (FIG. 1B). The holder 120 may be formed of a generally rigid material including, without limitation, a plastic or metal.

Figure 5B:
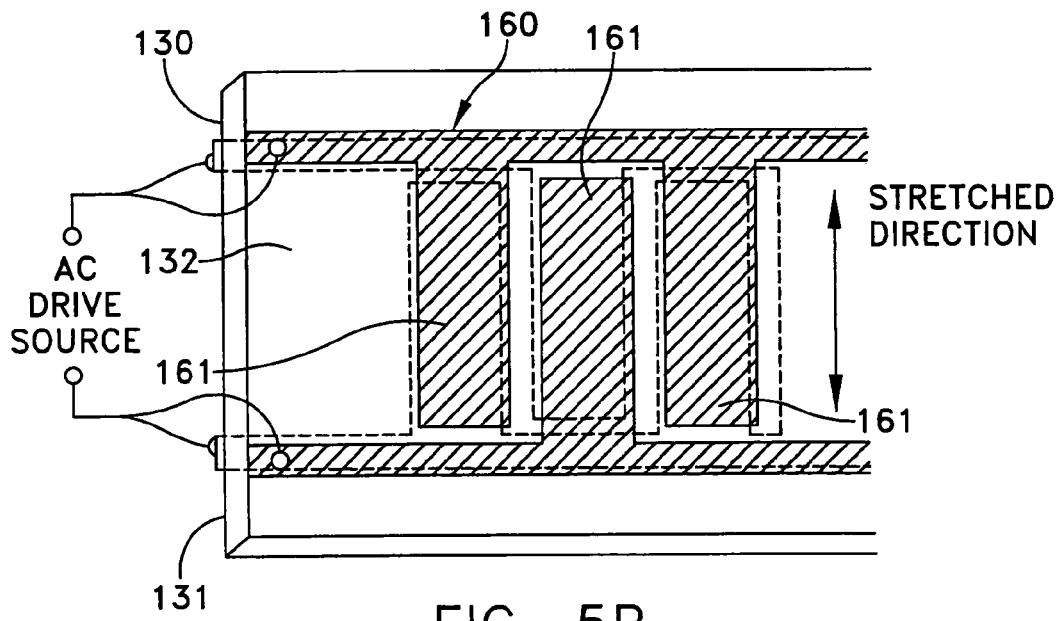
FIG. 5B is an enlarged elevational view of a portion of the piezoelectric transducer film shown in FIGS. 1B–1E prior to being formed into a cylinder.

FIG. 5B is an enlarged view of the piezoelectric transducer film 130 prior to being formed into a cylinder. The earlier described segmented electrode patterns 160 are formed on the outer and inner surfaces 131, 132 of the piezoelectric transducer film 130 prior to forming the transducer film 130 into a cylinder.

Figure 5C:
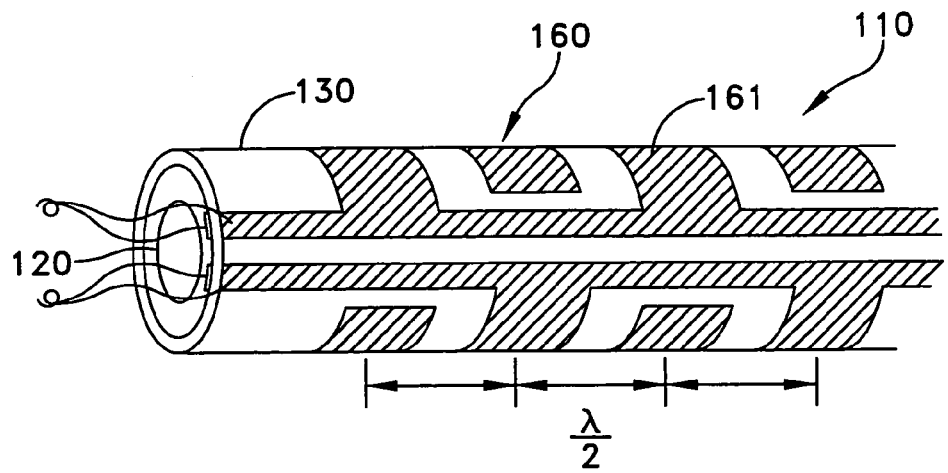
FIG. 5C is an enlarged view of the MSCUT shown in FIGS. 1B–1E.

FIG. 5C is an enlarged view of the transducer 110 showing the piezoelectric transducer film 130 cylindrically wrapped around the holder 120. Once wrapped, the ends of the piezoelectric transducer film 130 are secured to one another using any suitable means, including without limitation, an adhesive, and preferably, by ultrasonically welding the ends to one another. Note that the periodicity of each electrode segment 161 is chosen to be about one-half wavelength.

Figure 6:
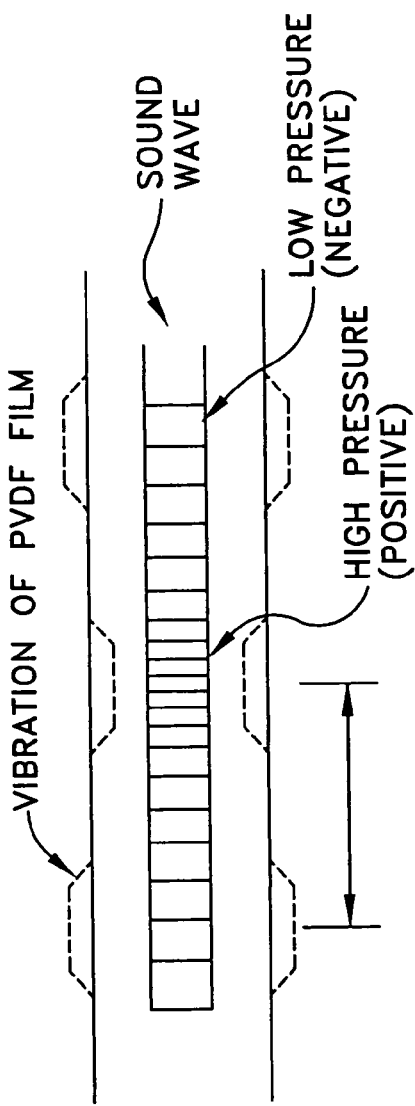
FIG. 6 is a schematic illustration showing the vibration phases of the MSCUT of FIGS. 1B–1E.

Referring to FIGS. 5B and 5C, the excitation voltage V is applied to the electrode segments 161 in a manner wherein the phase of the voltage applied to each electrode segment 161 alternates from one segment 161 to another. This causes the transducer 110 to produce vibration phases that are opposite to one another, as shown in FIG. 6. The vibration of the transducer film 130 induces pressure variation in the transducer 110, which varies along the longitudinal direction of the transducer 110. When the selected excitation voltage with frequency Vs/2f (where Vs is the excitation voltage and f is the frequency) is equal to the $\lambda/2$ periodicity, (i.e., one-half wavelength), acoustic waves are generated by the transducer 110. The acoustic waves propagate along the longitudinal axis of the transducer 110 in both directions, as shown in the sectional view of FIG. 7.

Figure 7:
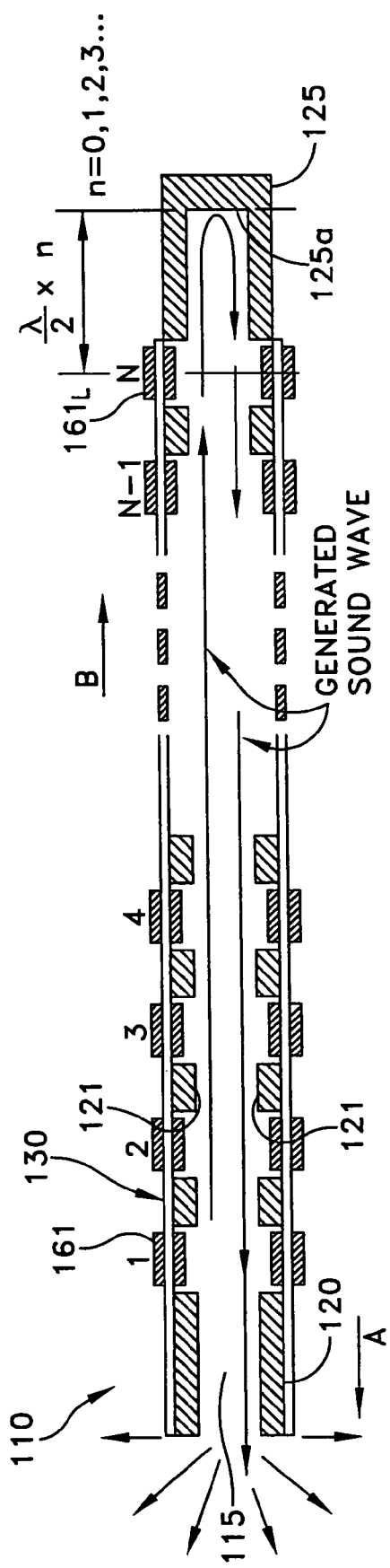
FIG. 7 is a sectional view of the MSCUT shown in FIGS. 1B–1E provided with a reflector.

Referring still to FIG. 7, a reflector 125 may be provided at one end of the transducer 110. As shown, the transducer 110 generates first and second acoustic waves propagating in opposite longitudinal directions indicated by arrows A and B. The first acoustic wave propagating in the direction of arrow A, exits from the opening 115 of the transducer 110, and the second acoustic wave propagating in the direction of arrow B is reflected by the reflector 125 (back down the transducer 110 in the direction of arrow A). The reflector 125 should be positioned so that its reflecting surface 125a is spaced from the center of the last electrode segment $161_L$ by a distance equal to $n\lambda/2$ the periodicity where n is an arbitrary integer so that the reflected second acoustic wave now propagating in the direction of arrow A is superposed in-phase with the first acoustic wave propagating in the direction of arrow A. Note that the inner diameter of the transducer 110 is selected to be smaller than one-half wavelength, the acoustic waves diverging to a space with little angular dependence. The output power of the transducer 110 can be increased by the periodic structure 161, but, the bandwidth becomes smaller. The bandwidth is approximately given by $$\Delta f = f_o/(N/2),$$

where $f_o$ is the center frequency and N is the total number of the electrode segments 161. Similarly, the output power of the transducer 110 can be decreased by reducing the number of electrode segments 161. In one embodiment of the invention, the transducer 110 may include only one electrode segment 161, which is the case of N=1.

Figure 8:
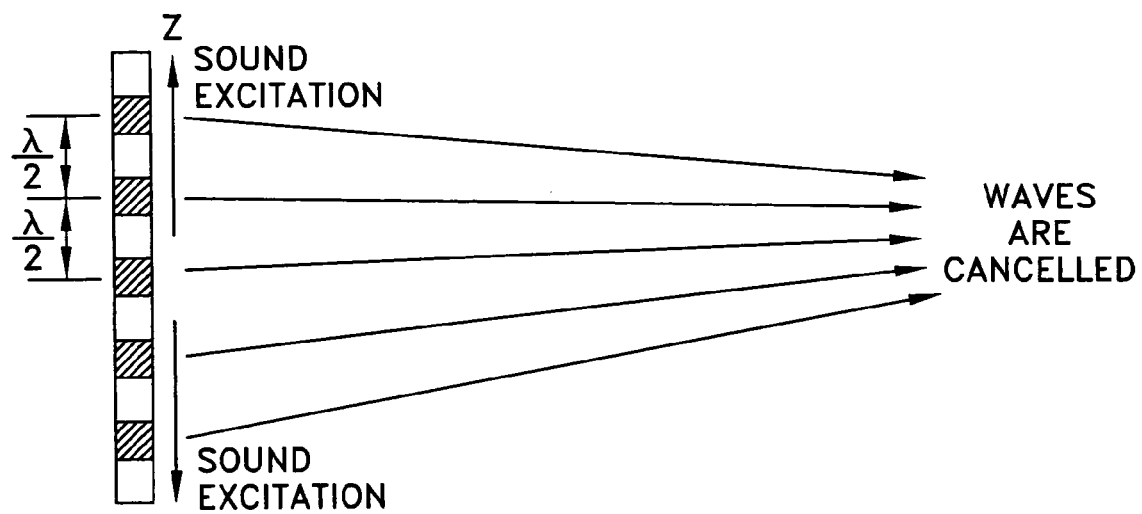
FIG. 8 is a schematic illustration showing how acoustic signals are generated and propagate from the MSCUT of the invention.
Figure 9:
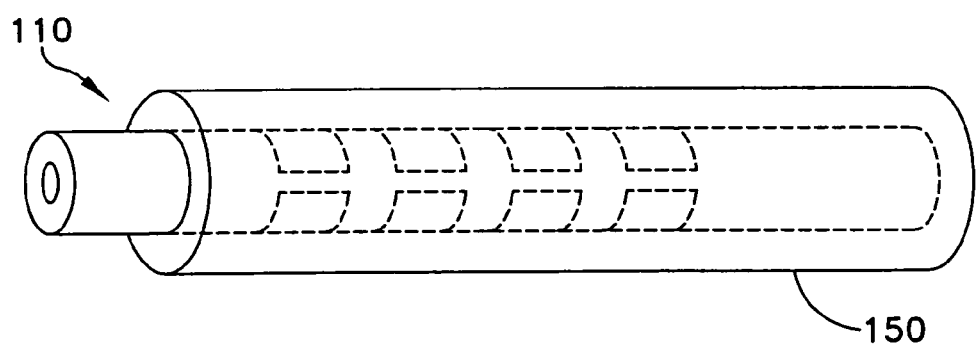
FIG. 9 is an enlarged perspective view of the MSCUT structure shown in FIG. 1D.

The transducer 110 generates acoustic signals which propagate toward the axial direction Z, as shown in FIG. 8. Therefore the transducer 110 may be covered by the earlier described cover 150 as shown in FIG. 9.

FIGS. 10A and 10B collectively illustrate another embodiment of a handheld stylus 400 utilizing a cylindrical transducer according to a further embodiment of the invention, denoted by numeral 510. The stylus 400 comprises a housing 410 defining an internal bore 420 having opening 420a for receiving a drawing implement 430. The transducer 510 comprises a cylindrical piezoelectric PVDF transducer film 530 of radius R and length L disposed about a spool-shape portion 520 (shown with broken lines) of the drawing implement 430, the spool-shape portion 520 being located within the housing 410 of the stylus 400. The outer and inner surfaces 531, 532 of the transducer film 530 each include a ring-shape electrode layer 561. The electrode layer 561 on the inner surface of the transducer film 530 may be at ground or reference potential, while the electrode layer 561 on the outer surface of the transducer film 530 may have applied thereon a voltage V. The opening 420a of the housing bore 420 provides a pathway for the propagation of an acoustic signal generated by the transducer 110 in an axial direction of the stylus 400. The ring width w of each electrode layer 561 is about equal or less than one-half wavelength. When the electrode layers 561 have a width of greater than one-half wavelength, the acoustic waves emanating from points that are more than one-half wavelength apart relative to one another operate to cancel each other. In this case, acoustic signals, denoted by A and B, are radiated in two opposite directions, as shown in FIG. 10B.

Figure 10C:
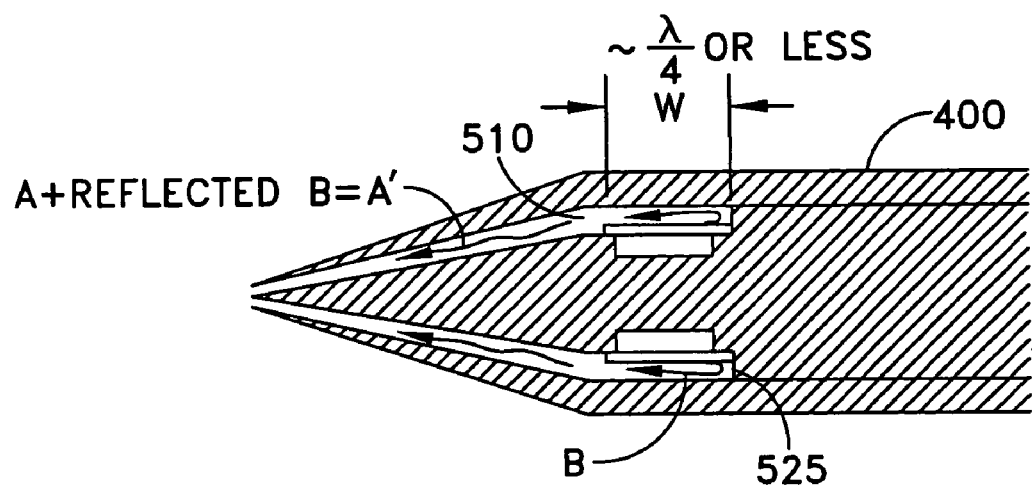
FIG. 10C is a sectional view of a portion of the MSCUT shown in FIGS. 10A and 10B provided with a reflector.

FIG. 10C shows the stylus 400 and transducer 510 shown in FIGS. 10A and 10B combined with a reflector 525, which is mounted at the end of the transducer 510 to reflect the acoustic wave B back in the direction of acoustic wave A, so that both may be used effectively. This reduces power consumption by a factor of 2 while maintaining substantially the same output signal strength. Note that the ring width of the electrode layer 561 is about one-quarter wavelength or less in this embodiment.

Figure 10D:
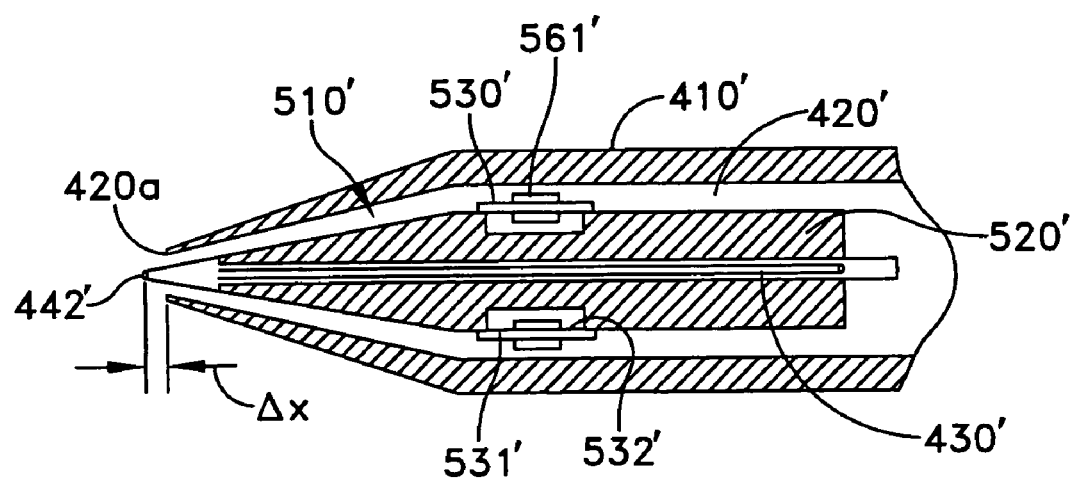
FIG. 10D is a sectional view of another embodiment of a handheld stylus which utilizes another embodiment of a MSCUT according to the invention.

FIG. 10D shows another embodiment of a stylus 400' utilizing a cylindrical transducer according to another embodiment of the invention, denoted by numeral 510'. The stylus 400' comprises a housing 410' defining an internal bore 420' having opening 420a' for receiving a drawing implement 430' having a drawing tip 442' extending only a slight distance Δx from the plane of the opening 420a'. The transducer 510' comprises a cylindrical piezoelectric PVDF transducer film 530' disposed about a spool-shape mandrel or holder 520' located within the housing 410' of the stylus 400'. The holder 520' includes an orifice 526' that extends the length of the holder 520', and which is sized to accommodate the drawing implement 430' therethrough. The outer and inner surfaces 531', 532' of the transducer film 530' each include a ring-shape electrode layer 561'.

FIGS. 11A–11C collectively illustrate another embodiment of a handheld stylus 600 utilizing a transducer structure according to another embodiment of the invention, denoted by numeral 700. The stylus 600 comprises a housing 610 defining an internal bore 620 having, opening 620a for receiving a drawing implement 630. The transducer structure 700 comprises concentric inner and outer transducers 710 and 710'. The inner transducer 710 includes a first cylindrical piezoelectric PVDF transducer film 730 of radius $R_1$ disposed about a spool-shape portion 720 (shown with broken lines) of the drawing implement 630, the spool-shape portion 720 being located within the housing 610 of the stylus 600. The outer and inner surfaces 731, 732 of the first transducer film 730 each include a ring-shape electrode layer 761. The outer transducer 710' includes a second cylindrical piezoelectric PVDF transducer film 730' of radius $R_2$ disposed over an inner surface portion 720' (shown with broken lines) of the housing 610, the inner surface portion 720' being located within the housing 610 of the stylus 600 and defining an annular recess 721'. The outer and inner surfaces 731', 732' of the second transducer film 730' each include a ring-shape electrode layer 761'.

Both transducer films 730, 730' are electrically connected in parallel, however, the relation between film polarity and electric field direction is selected such that the displacement of one film is in the direction opposite to that of the other film. In other words, when one film shrinks in vibration, causing its diameter to decrease, the other film expands in vibration, causing its diameter to increase. An air gap g defines the space between the two transducer films 730, 730', the air between the films 730, 730' being effectively driven in the axial direction. The ring widths w of the electrode layers 761, 761' on the corresponding transducer films 730, 730' are about equal or less than one-half wavelength.

Figure 11D:
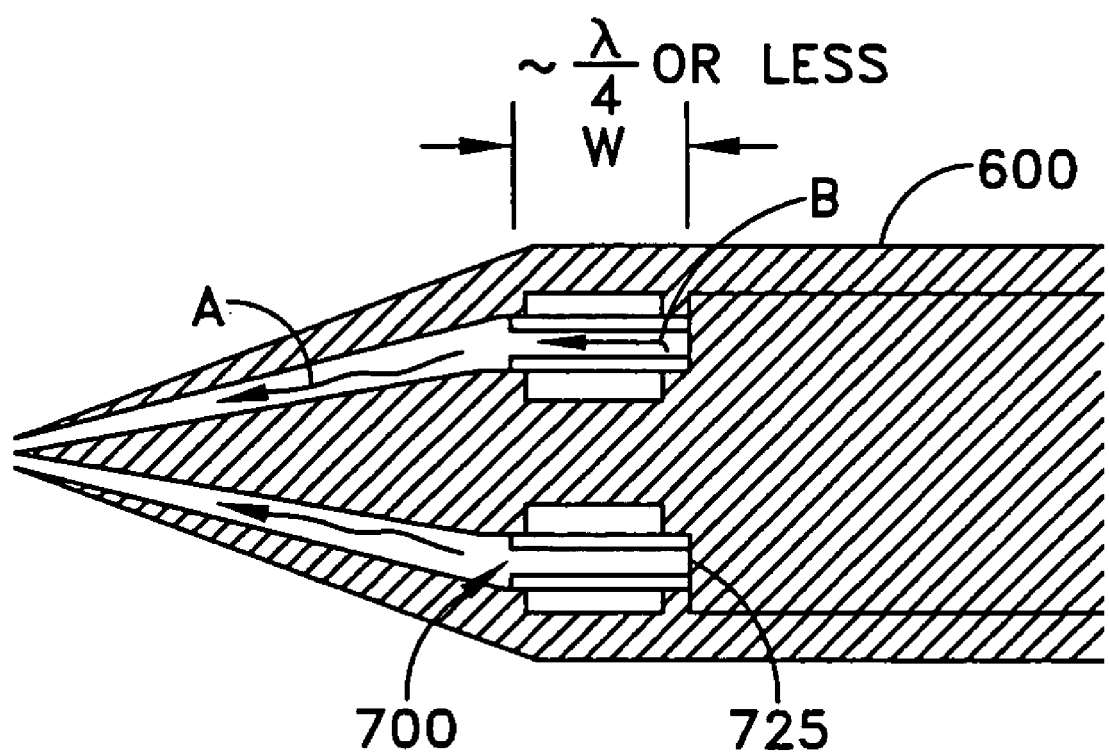
FIG. 11D is a sectional view of a portion of the MSCUT shown in FIGS. 11A–11C provided with a reflector.

FIG. 11D shows the stylus 600 and concentric double film transducer structure 700 of FIGS. 11A–11C having a reflector 725 mounted at the end of the transducer structure 700 to reflect the acoustic wave B back in the direction of acoustic wave A, so that both may be used effectively. By this structure, both advantages of a concentric film structure and an in-phase addition of the reflected wave are combined. Note that the ring width of the electrode layers 761 is about one-quarter wavelength or less in this embodiment.

Figure 12:
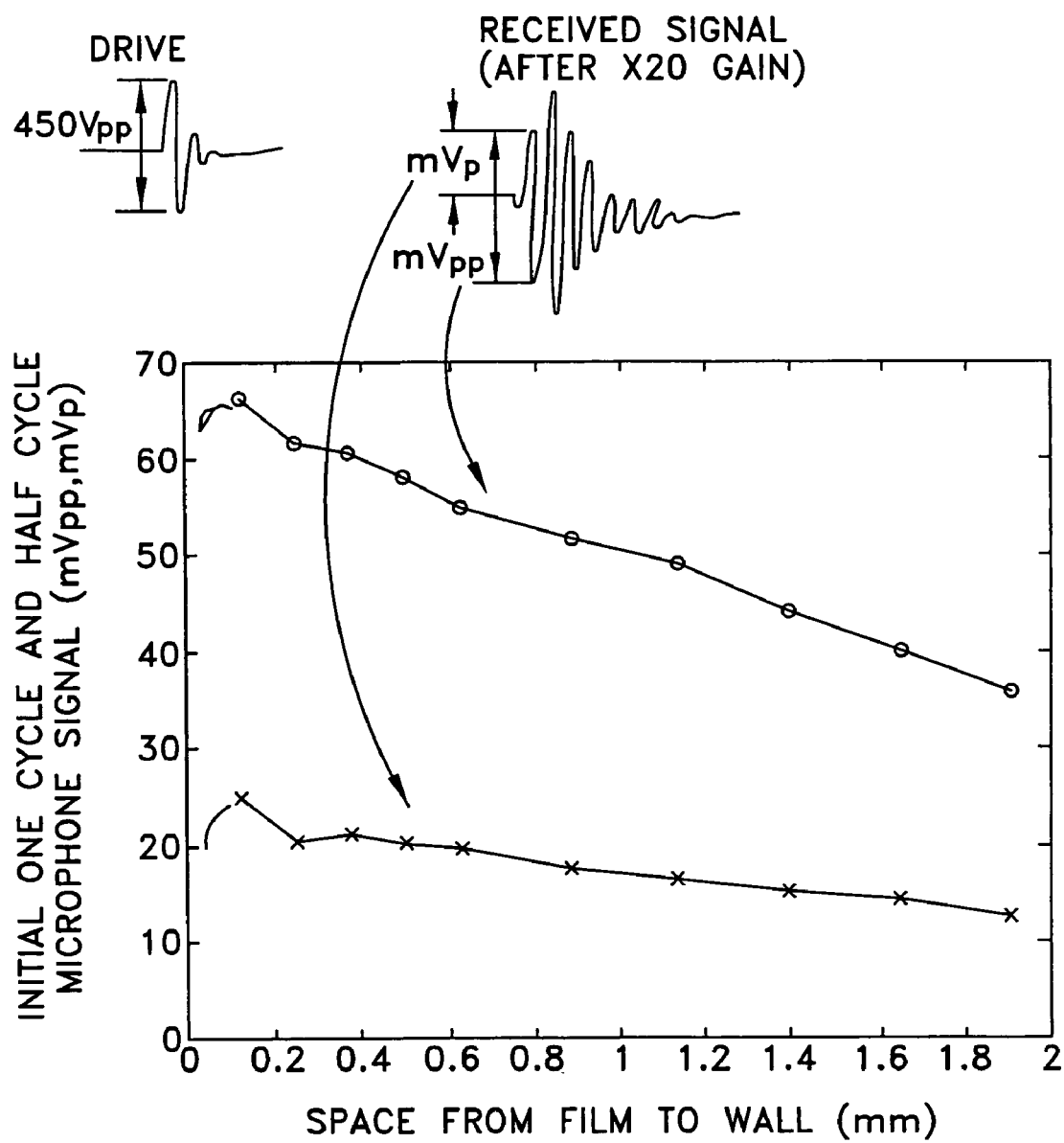
FIG. 12 is a plot of acoustic output signal strength as a function of space from the transducer film surface to the interior wall of the stylus housing.
Figure 13A:
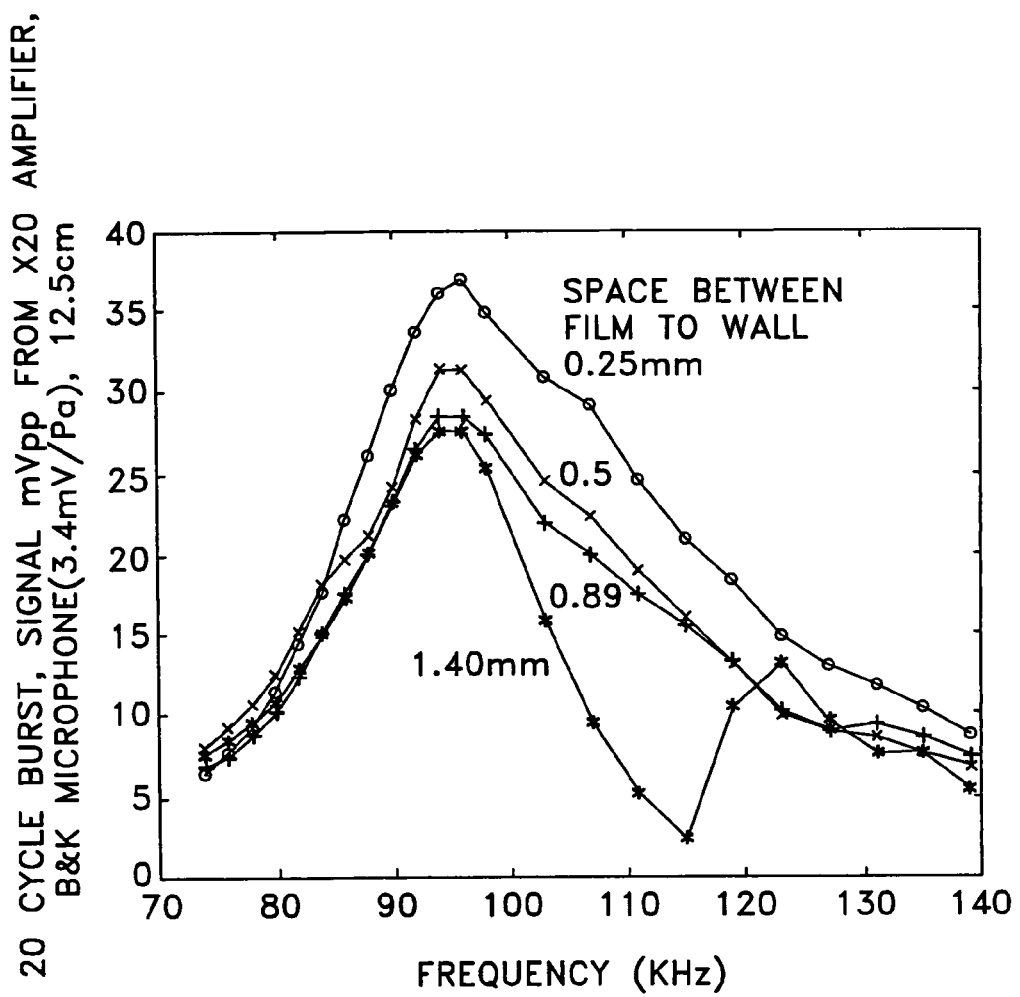
FIG. 13A is a plot of the signal strength as a function of frequency for various film-housing spacings.
Figure 13C:
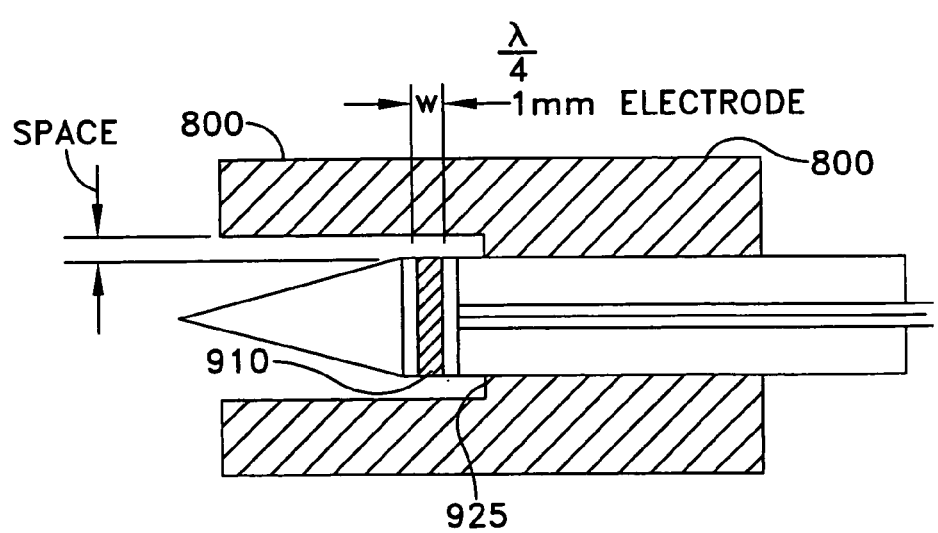
FIG. 13C is a sectional view showing a handheld stylus similar to that shown in FIG. 10C, which was used for the plots of FIGS. 12, 13A and 13B.
Figure 13B:
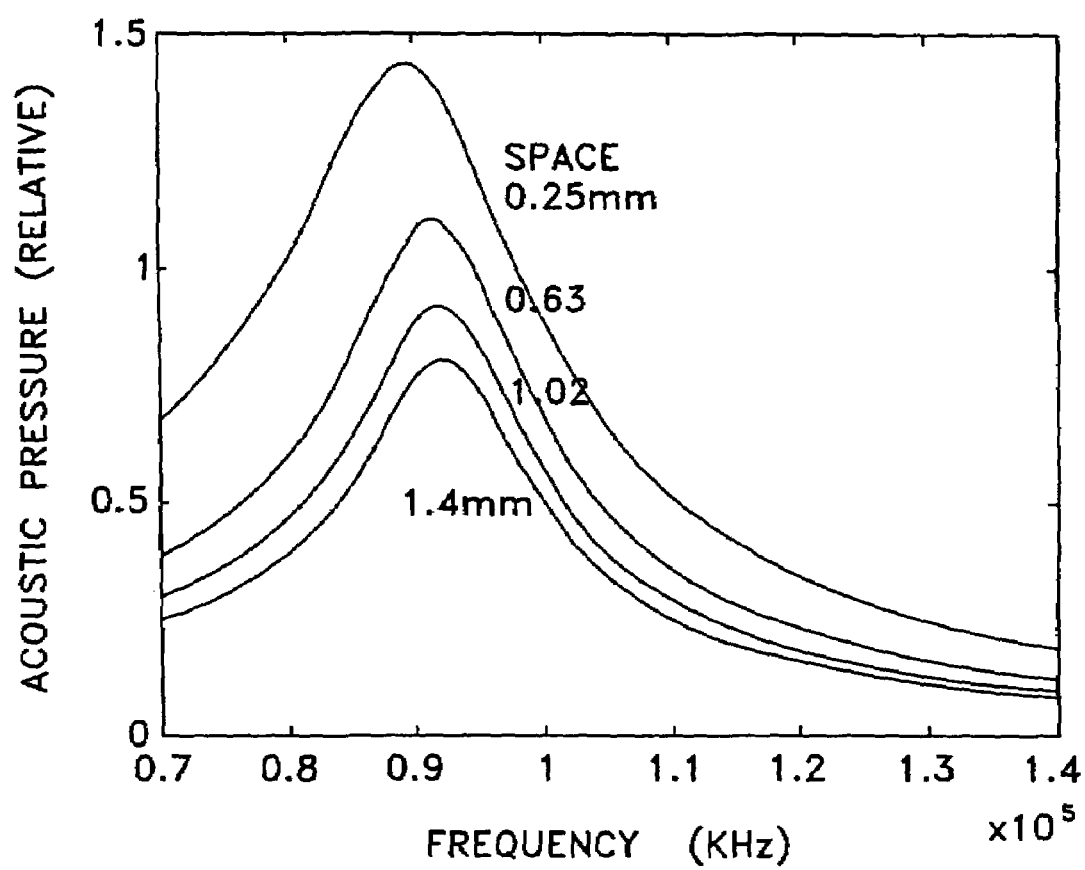
FIG. 13B is a theoretical plot showing the signal strength as a function of frequency for various film-housing spacings.

FIG. 12 provides a plot of acoustic output signal strength as a function of space from the transducer film surface to the interior wall of the stylus housing while FIG. 13A plots the signal strength as a function of frequency for various film-housing spacings. FIG. 13C shows a stylus 800 and transducer 910 similar to that shown in FIG. 11C, which was used for the plots of FIGS. 12, 13A and 13B. Better impedance matching to air explains the increased output for a narrower space S (FIG. 14C) as shown in the theoretical plot of FIG. 14B.

Figure 14A:
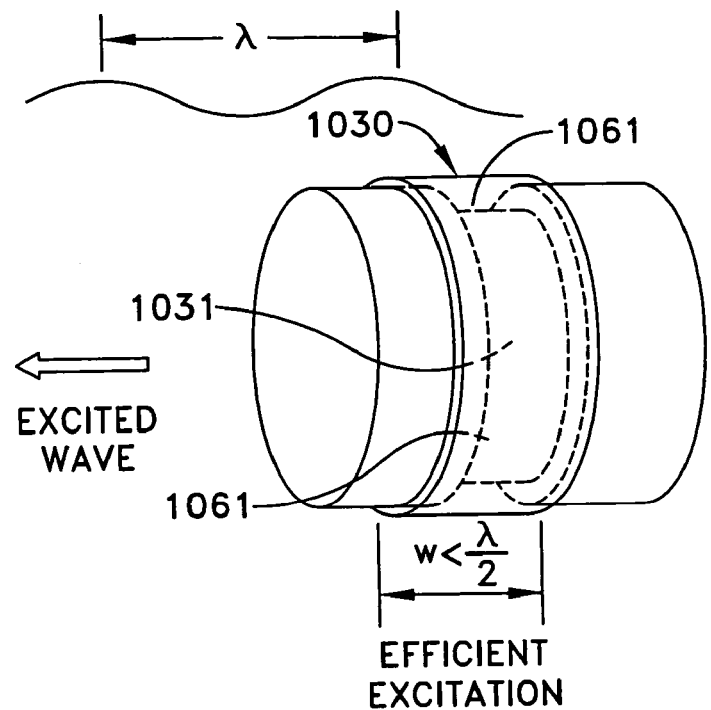
FIGS. 14A and 14B are perspective views each showing a cylindrical piezoelectric transducer film having a ring electrode disposed on each of the outer and inner surfaces of the film.
Figure 14B:
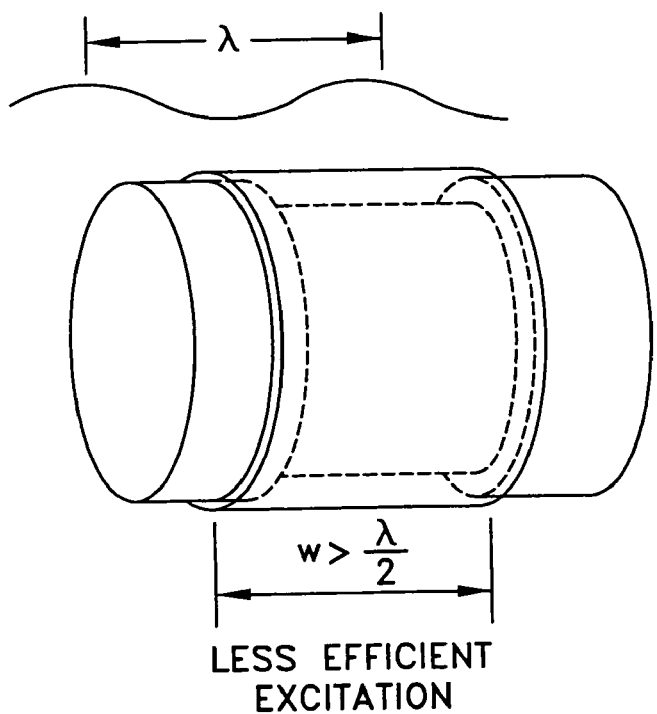

Another aspect of the invention comprises a driving mechanism, which may be used for driving the cylindrical ultrasonic transducer structures described earlier herein. FIG. 14A shows a cylindrical piezoelectric transducer film 1030 made from a PVDF material, for example, having a ring electrode 1061 disposed on each of the outer and inner surfaces 1031, 1032 of the film 1030. The cylindrical transducer film 1030, in response to electrical excitation, generates an acoustic wave propagating in the axial direction. The ring width w of each electrode 1061 has to be equal or less than one-half wavelength. If, as shown in FIG. 14B, the ring width w is more than one-half wavelength, the excited wave in the axial direction becomes weaker because the phase of excitation does not match with the propagating wave, thereby partially canceling the signal.

Figure 15:
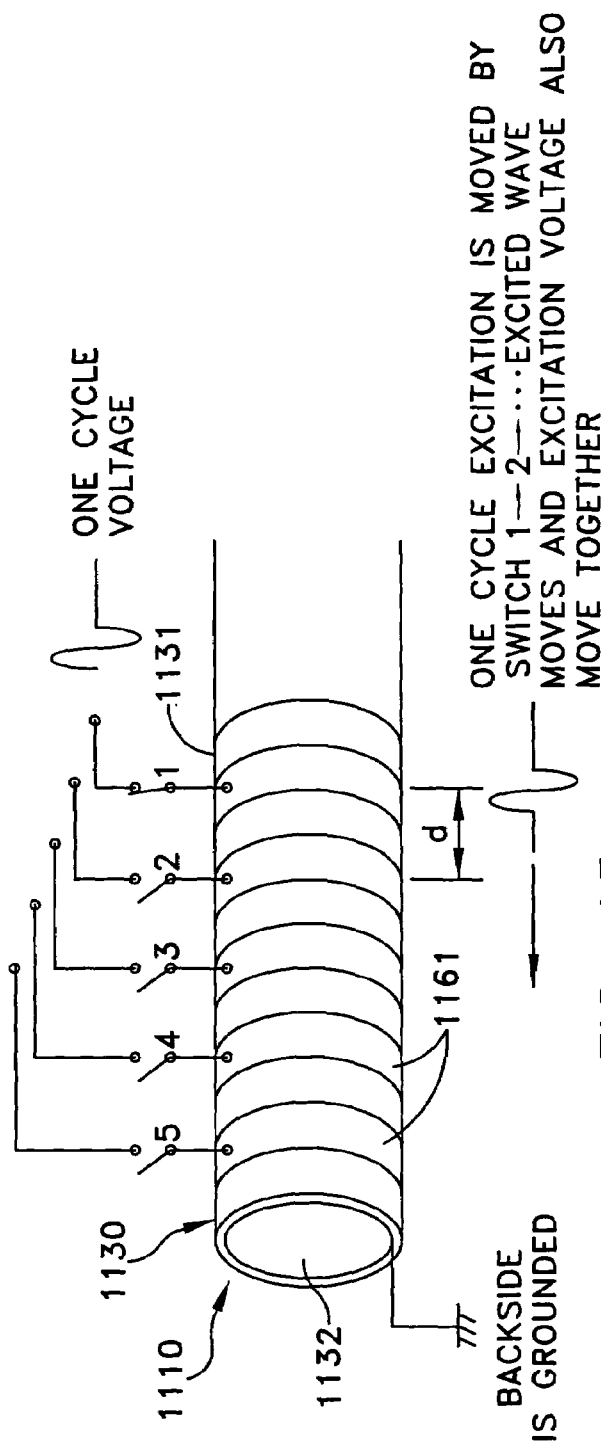
FIG. 15 is a perspective view of an embodiment of a sequentially driven multiple ring electrode cylindrical transducer made according to the invention.

In order to enhance the axial acoustic wave excitation, there is shown in FIG. 15 an embodiment of a sequentially driven multiple ring electrode cylindrical transducer 1110 made according to the principles of the invention. The transducer 1110 comprises a cylindrical piezoelectric transducer film 1130 made from a PVDF material, for example, having multiple ring electrodes 1161 disposed on the outer surface 1131 thereof, and a common ground on the inner surface 1132 thereof. The operation of such device is as follows. First, one of the ring electrodes 1161 on the outer surface 1131 of the film 1130 is driven. Second, an adjacent second one of the ring electrodes 1161, located in the direction of and, therefore, in front of the propagating acoustic wave, is driven with a time lag, relative to the first driven electrode 1161. The time lag is given by $T=d/V_s$ where d is the center to center distance of the two adjacent ring electrodes 1161 and $V_s$ is the propagation velocity in air. The third, fourth, fifth, etc . . . electrodes 1161 are then sequentially driven. During the time T, the acoustic wave proceeds by distance d and the relationship between the drive voltage and the excited acoustic wave, are the same for each electrode 1161. The one-cycle-drive is then sequentially applied to the next electrode pair and the driven voltage moves with the same speed as the wave propagates. Thus, a single cycle acoustic wave increases in strength after the aforementioned series of excitations. Note here that the film cylinder has its own resonance and "one cycle drive" means, at a first half cycle a displacement is given to the film and at a next half cycle, the film displaces to the opposite direction (kick back) with its own resonance behavior, and at this time the drive voltage provides an opposite sign of voltage compared with the initial half cycle, and this forced drive and its own displacement are in an in-phase condition. Therefore, the displacement of the initial half cycle is very small but, the next half cycle is much larger and this larger displacement is used as the signal. To aid in understanding this, consider the following analogy involving the swinging of a child swing. At first you push the swing with a small force, which does not cause much of a swing action, but when the swing comes back, you pull it, and then, the swing action becomes larger the second time.

Figure 17:
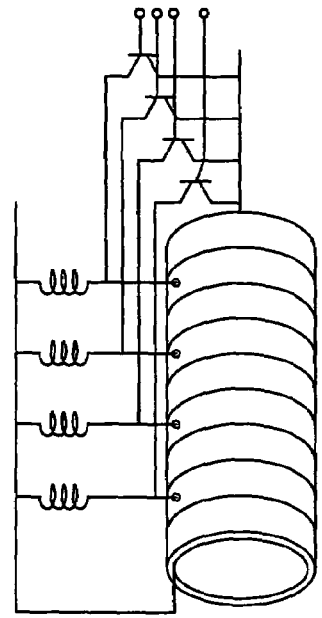
FIG. 17 is a schematic illustration showing an exemplary embodiment of how the amplifiers of FIG. 16 may be associated with the ring electrodes of the transducer shown in FIG. 15.
Figure 16:
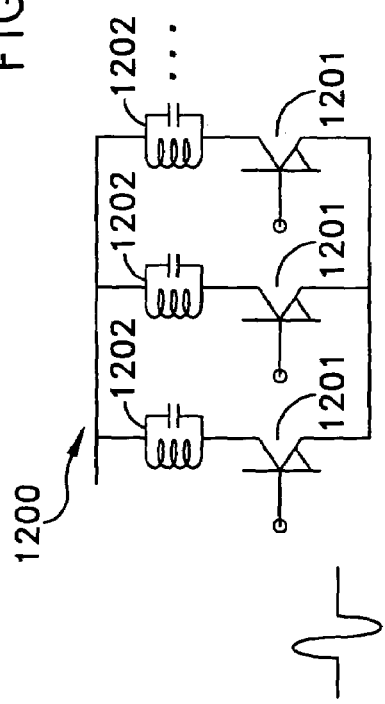
FIG. 16 is a schematic illustration of an embodiment of a drive circuit according to the invention, for driving the multiple ring electrode cylindrical transducer shown in FIG. 15.

FIG. 16 is a schematic illustration of a drive circuit 1200 comprising multiple drive amplifiers 1201 for driving the multiple ring electrode cylindrical transducer of FIG. 15. In an exemplary embodiment as shown in FIG. 17, each amplifier 1201 is associated with one of the ring electrode 1161 such that, if four electrode rings 1161 are used, four independent drive amplifiers 1201 are used. Each amplifier 1201 has a resonant inductive coil 1202 to provide a high drive voltage. Each drive amplifier is driven with a predetermined sequential delay, given by T=d/Vs.

Figure 18:
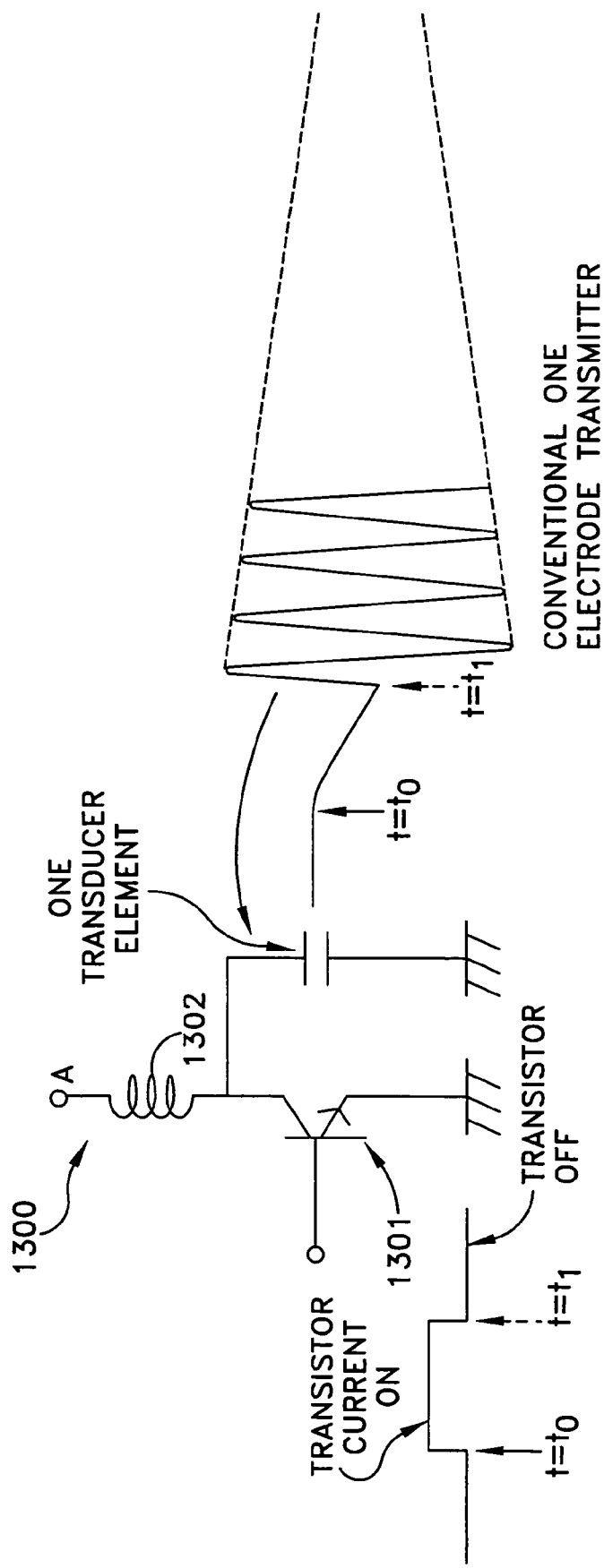
FIG. 18 is a schematic illustration of an alternate embodiment of a drive circuit according to the invention, as used for driving a single ring electrode cylindrical transducer.

In an alternative embodiment, as shown in FIG. 18, a switched resonator circuit 1300 may be used as the drive circuit. This is advantageous, since the drive circuit 1200 shown in FIG. 16 requires multiple resonant coils 1202 which tend to be bulky and expensive. The switch resonator circuit 1300 requires only one resonant coil 1302, and consumes much less power than drive circuit 1200 of FIG. 16. As shown in FIG. 18, the basic drive method for a one electrode transmitter is illustrated. As shown therein, after turning on a transistor 1301, a current flows through the circuit 1300. When the input voltage is turned on at $t=t_o$, the transistor current starts to flow and the voltage at node A of inductance and capacitance begins to decrease, ultimately reaching a negative minimum value. At this point ($t=t_1$), the current is shut off, and the voltage starts to sharply increase and then rises to a maximum value before decreasing again, and the voltage oscillates in an exponentially decaying sinusoidal waveform (ringing). The power consumption occurs only during the period from initial turn-on to shut off of the transistor (from $t=t_o$ to $t_1$).

Figure 19:
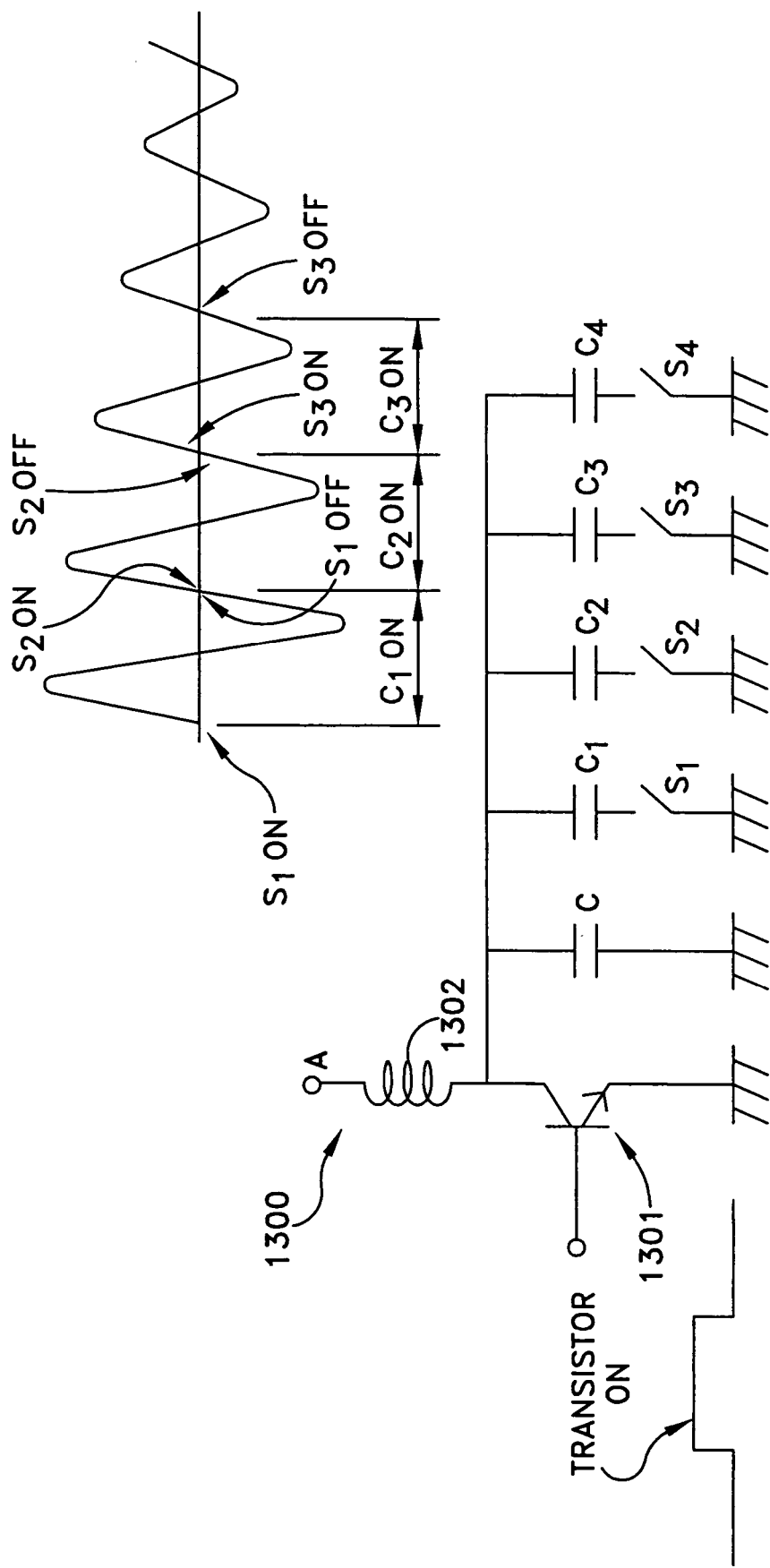
FIG. 19 is a schematic illustration of the drive circuit shown in FIG. 18 according to the invention, as used for driving a multiple ring electrode cylindrical transducer.

While the above method is used for a one ring electrode transducer, when the electrode is subdivided into multiple ring electrodes, the driving method is, in principle, the same. Referring to FIG. 19, the driving method commences with current flowing into the transistor 1301 until current is shut off. The inductance and capacitance then commences its ringing oscillation cycle. The voltage across the capacitor $C_1$ initially increases, and then, after one cycle it comes back to 0 volts. At this instant the first capacitor $C_1$ is disconnected from the circuit 1300 and the second capacitor $C_2$ is connected in circuit 1300. Although the first and second capacitors $C_1$, $C_2$ have been switched, such switching does not influence the resonant oscillation and ringing continues. Thus, the second capacitor $C_2$ has the voltage of the next one cycle swing. Hence, the voltage again comes to almost 0 volts. At this instant, the second capacitor $C_2$ is disconnected from the circuit 1300 and the third capacitor $C_3$ is connected in circuit 1300. In this way, every one cycle, voltage is applied to the next capacitor in the sequence. Every cycling oscillation, the peak voltage amplitude decreases slightly. In essence, the capacitors $C_1, C_2, C_3 \ldots$, each express one ring electrode on the transducer film, and multiple electrodes are sequentially driven by each cycle of ringing.

The decay rate depends on the loss associated with the capacitor. For a PVDF transducer film, the film is lossive with tan delta=0.1. In order to reduce the effective loss, a high quality capactior C shown in FIG. 19 is connected in parallel with the inductor 1302. The capacitor C is not switched. In this way, a very strong, single cycle wave is excited and propagates in the axial direction. The transducer of the invention mounted in the interior of the stylus housing generates an axial waveform, which propagates along the bore of the housing, until it reaches the housing opening. The opening is substantially co-located with the tip region of the drawing implement so that the ultrasound signal exiting from the opening reflects off the location of the drawing implement on the pen or stylus independent of the tilt angle of the stylus.

Figure 20:
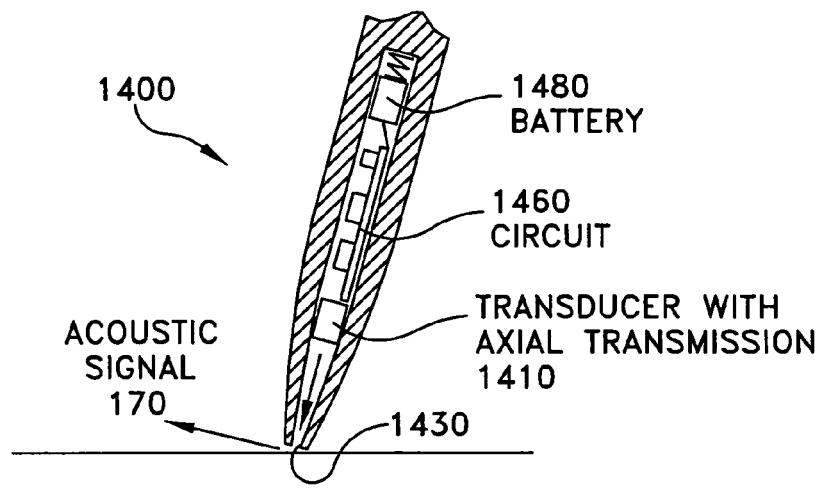
FIG. 20 is a schematic representation of a handheld stylus including a transducer, made according to the invention.
Figures 21A, 21B, 21C, 21D:
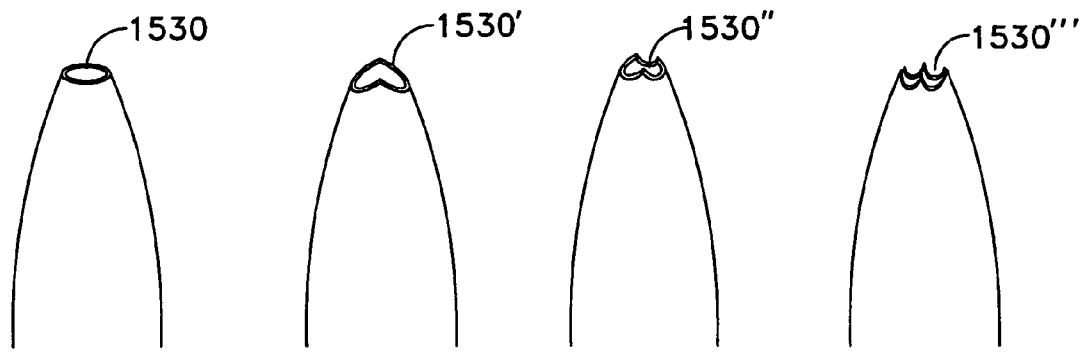
FIGS. 21A–21D illustrate exemplary stylus opening configurations according to the invention.

FIG. 20 is a schematic representation of a handheld stylus 1400 including a transducer 1410 made according the principles described herein having axial acoustic transmission characteristics, appropriate drive circuitry 1460 in electrical communication with the transducer 1410, and associated power supply or battery 1480 for powering the stylus 1400. It is understood that the embodiments of the invention described herein use well known circuitry and power sources for activating and maintaining the signal power to the invention.

FIGS. 21A–21D illustrate exemplary stylus opening configurations, respectively denoted by numerals 1530, 1530', 1530", and 1530'".

FIGS. 22 and 23 each show an embodiment of an electrode drive connection structure according to the invention, which may be used for connecting the ring electrodes to drive circuitry, where the backside electrode is common ground.

A further aspect of the invention comprises a flat ultrasonic transducer structure having axial acoustic transmission characteristics. The flat ultrasonic transducer structure of the invention is especially intended for use as an ultrasonic transmitter. However, one of ordinary skill in the art will appreciate that the flat ultrasonic transducer structure of the invention. may also be utilized as a receiver.

Referring now to FIG. 24A, there is shown an embodiment of a flat ultrasonic transducer according to the invention, denoted by numeral 2040. The flat ultrasonic transducer (FUT) 2040 comprises a thin, flat, diaphragm 2044 and a thin, flat, piezoelectric transducer film 2042 adhesively bonded to the diaphragm 2044. The diaphragm 2044 may comprise, without limitation, a metal, such as Aluminum (Al), and may be circular (as shown), square or rectangular in plan view. The Al-based diaphragm 2044 may have a thickness of about 0.1 mm–0.8 mm, depending on the diameter. The transducer material 2042 may comprise, without limitation, a piezoelectric ceramic, such as lead-zirconate-titanate (PZT), and may be circular (as shown), square or rectangular in plan view. The transducer 2042 may be a PZT-based transducer film 2042 and may have a thickness of about 0.1 mm–0.5 mm. The diameter of the diaphragm 2044 in this embodiment is larger than the diameter of the transducer material 2042. However, as shown in FIG. 24B, the transducer material 2042 may have a diameter which is substantially the same as the diameter of the diaphragm 2044. In addition, the FUT 2040 may be supported in an annular mounting member 2046 made from an acoustically lossy/flexible material. The mounting member 2046 supports front and back sides 2040a, 2040b of the FUT 2040.

Another aspect of the invention is a handheld stylus which may utilize the FUT of FIGS. 24A and 24B. Referring now to FIGS. 25A–25D there is collectively shown an embodiment of a handheld stylus according to the invention, denoted by numeral 2200. The stylus 2200 comprises a housing 2220 having a cylindrical body portion 2222 having an inner side surface 2228 and neck portion 2224 extending from the body portion 2222. The neck portion 2224 may comprise a solid member having a generally cone-shape outer surface, a generally planar end surface 2227 which is generally perpendicular to the body inner side surface 2228, and a centrally located, constant diameter bore 2226 that communicates with the external environment via an emitting opening 2221 of the stylus housing 2220 (neck portion 2224). The cylindrical interior 2229 of the body portion 2222 has a diameter which is substantially greater than the constant diameter of the bore 2226 for accommodating the FUT 2040 of FIG. 24A.

As shown in FIG. 25A, the FUT 2040 is mounted perpendicular to the longitudinal axis LA of the stylus housing 2220 across the cylindrical interior 2229 of the body portion 2222, in axial alignment with the bore 2226 and the body portion 2222. The FUT 2040 is constructed with the earlier-described circular transducer material 2042 and corresponding circular diaphragm 2044. The face of the FUT diaphragm 2044 is seated against a rigid, continuous or segmented annular shoulder 2225 defined on the body inner side surface 2228 of the body portion 2222, the diaphragm 2044 of the FUT 204 being sized such that its peripheral edge engages the cylindrical body inner side surface 2228. The rigid shoulder 2225 can also be replaced by an acoustically lossive material. The shoulder 2225 is located within the body portion 2222 so as to define a narrow gap G between the FUT 2040 and the planar end surface 2227 of the neck portion 2224. The FUT 2040 may be securely retained in position within the interior 2229 of the body portion 2222 by an arrangement comprising an annular flexural coupler 2245 made from rubber or some other acoustically lossy/flexible material, and a rigid, annular support member 46. The coupler 2245 and the support member 2246 are wedged between face 2040b of the FUT diaphragm 2044 and annular detent 2228a defined on the body inner side surface 2228, so as to urge the FUT diaphragm face 2040a against the shoulder 2225 defined on the body inner side surface 2228 of the body portion 2222.

Still referring to FIG. 25A, electrodes $e_1$, $e_2$ in contact with front and back surfaces of transducer material 2042 of the FUT 2040, drive the ultrasound transmitter with an AC signal to generate an acoustic signal S output from the FUT 2040 which propagate down the central bore 2226, as will be explained in greater detail further on, and exiting at an emitting opening 2221 of the stylus housing 2220. A writing and drawing implement 2250 having a tip 2251 including, without limitation, an ink cartridge, extends partially through the central bore 2226. The tip 2251 of the drawing implement 2250 extends a short distance out from the emitting opening 2221 of the stylus housing 2220. A switch 2254 including, without limitation, a microswitch, and associated stopper member 2255 that limits longitudinal motion of the implement 2250 toward gap G, are disposed at the end of the implement opposite the tip 2251. The switch 2254 detects contact between the tip 2251 of the implement 2250 and a writing or drawing surface (not shown). When contact is detected, the switch 2254 activates the FUT 2040 to generate acoustic signals in response to the detected contact. Switches that activate/deactivate ultrasonic transmitter/receiver devices in response to a change in force applied by or to a writing and drawing implement indicative of contact with a writing or drawing surface, are well known in the art and, therefore, will not be described in further detail herein.

The central bore 2226 has a relatively much small diameter d (FIG. 25B) as compared to the diameter of the vibrating area of the transducer material 2042 and is substantially coaxial with the FUT 2040. As shown in FIG. 25B-25D, the portions of the bore 2226 not occupied by the implement 2250, switch 2254, and stopper 2255, operate as a waveguide for the propagating acoustic wave or signal output generated from the FUT 2040. The acoustic waves or signal generated by the FUT 2040 propagates through the narrow gap G at the front of the vibrating diaphragm 2044 and is guided down the central waveguide bore 2226. The engagement between the peripheral edge of the FUT 2040 and the inner side surface 2228 of the housing body portion 2222 creates a seal, which forces the acoustic waves to propagate through the waveguide bore 2226.

Referring again to FIG. 25A, the front air space or gap G has a function of impedance matching, wherein the gap G is formed relatively narrow and should be relatively small for a high frequency acoustic signal (e.g. 0.2–0.8 millimeters (mm) for 40 KHz signal, L/40 to L/10 where L=wavelength and at 80 KHz the gap become half) to obtain a higher output by making the space narrower.

It is contemplated that the FUT may also be implemented as an electro-static transducer, a curved PVDF film transducer having both PVDF film ends clamped, or a clamped, corrugated PVDF film transducer.

An alternative embodiment of the stylus of the invention is shown in FIG. 26A-26D, where like parts are indicated by like reference numerals. This embodiment is similar to that described with respect to FIGS. 25A–25D, however, as shown, the waveguide bore 2226' defined by the neck portion 2224 has a diameter which gradually decreases as the waveguide bore 2226' extends from the body portion 2222 towards the emitting opening 2221 of the stylus housing 2220 (neck portion 2224), thereby forming a horn-shape structure in FIG. 26A. Hence, an acoustic signal output from the FUT 2040 couples to the horn-shape waveguide bore 2226' and propagates to the emitting opening 2221 of the stylus housing 2220. In this embodiment, the function of impedance matching by a small gap G is lost, however, the coupling efficiency is improved, particularly when the acoustic signal wavelength is relatively short compared with the diameter D of the transducer material 2042 of the FUT 2040.

Referring again to FIG. 25A, the acoustic signal generated by the FUT 2040 propagates radially inward toward the space denoted by C as it crosses the gap G in the front of the FUT 2040. Since vibration is in-phase throughout the diaphragm area (i.e., the surface area of the diaphragm 2044), and the acoustic wave or signal must propagate in the gap G towards center, the phase relation between the acoustic signal and diaphragm vibration is different for the central region C and the peripheral region P. The difference at the center and periphery is approximately 180 degrees for a typical 40 KHz FUT having a diaphragm diameter of about 8 mm. Since vibrations are strong at the center and weaker at the periphery of the FUT 2040, the acoustic wave is not completely canceled during propagation, causing some cancellation of the signal. These problems become more severe at higher frequencies when the diameter of the diaphragm 2044 is not relatively small compared with the wavelength. The horn-shaped waveguide bore 2226' of the embodiment shown in FIGS. 26A–26D, tends to alleviate this problem.

FIG. 27A shows another embodiment of a handheld stylus 2300 according to the invention, comprising a FUT 2040 disposed (within the stylus housing 2320) parallel within the longitudinal axis LA of the stylus housing 2320. The FUT 2040 used in this embodiment as well as the embodiments which follow, employ the earlier-described rectangular or square transducer material 2042 and corresponding rectangular or square diaphragm 2044.

Referring again to FIG. 27A, activation of the transducer material 2042 bonded to the diaphragm 2044 causes vibration of the diaphragm 2044, which generates an acoustic signal S in the radial outward direction A that subsequently propagates through narrow gap G (defined between the FUT 2040 and wall w opposite thereto) in the direction of path L. In a preferred embodiment, the path length L is less than one half of the wavelength of the propagating acoustic signals. The resulting signal further propagates down the waveguide bore 2326 and exits at the emitting opening 2321 of the stylus housing 2320. Note that, as discussed above with respect to FIGS. 25A–25D, the narrow gap G plays the role of impedance matching, with the depth 0.2 mm–0.8 mm for 40 KHz of gap G being less than the diameter 2.5 mm–3 mm of the waveguide bore 2326.

FIG. 28 shows another embodiment of a handheld stylus 2400 according to the invention, wherein a pair of FUTs $2040_1$, $2040_2$ are disposed opposite one another within the stylus housing 2420, and parallel with the longitudinal axis LA of the stylus housing 2420. The purpose of the structure in FIG. 28 is that each of the FUTs 2040$_1$, 2040$_2$ faces back to air space, and are identically configured and driven to vibrate in opposite phase to one another so as to effectively double the acoustic pressure generated within narrow gap G formed between the diaphragms 2044$_1$, 2044$_2$ of the FUTs 2040$_1$, 2040$_2$. The acoustic waves subsequently propagate through narrow gap G in the direction of path L and through the waveguide bore 2426, thereby doubling the output at the emitting opening 2421 of the stylus housing 2420. The length of path L should be less than one-half the wavelength of the acoustic signal from each FUT 2040$_1$, 2040$_2$. Note that each of the FUTs 2040$_1$, 2040$_2$ are retained by clamping members 2445, which prevent the acoustic waves that are generated in respective back cavities B$_1$, B$_2$ from leaking into the narrow gap G where the acoustic signal is generated.

FIGS. 29A–29D collectively show another embodiment of a handheld stylus 2500 according to the invention, comprising a FUT 2040 disposed (within an interior 2539 of the stylus housing 2520) parallel with the longitudinal axis LA of the stylus housing 2520. The FUT 2040 outputs a first acoustic signal S1 from a front narrow gap G and a second acoustic signal S2 from a rear narrow gap G'. The first acoustic signal propagates down a first waveguide bore 2526a that communicates with the front narrow gap G and the second acoustic signal propagates down a second waveguide bore 2526b that communicates with the back narrow gap G'. The waveguide bores 2526a, 2526b merge together immediately adjacent to the emitting opening 2521 of the stylus housing 2520.

As shown in FIG. 29A, the first acoustic signal S1 generated by the FUT 2040 is directed toward a front wall F of the front narrow gap G that propagates along the path defined by the front narrow gap G formed between the FUT 2040 and the front wall F. The signal S1 exits front narrow gap G at an aperture 2502$_F$ formed in the front wall F and propagates down the first waveguide bore 2526a. In similar fashion, the second acoustic signal S2 generated by the FUT 2040 is directed toward a back wall B of the back narrow gap G' that propagates along the path defined by back narrow gap G' formed between the FUT 2040 and the back wall B. The signal S2 exits back narrow gap G' at an aperture 2502$_B$ formed in the back wall B and propagates down the second waveguide bore 2526b. The acoustic waves output from both the front and back sides of the FUT 2040 have essentially the same amplitude, but, are of opposite phases (i.e. 180 degrees out of phase with one another). In order to enable the signals S1, S2 output from the first and second waveguide bores 2526a and 2526b to constructively interfere, the path length P1 of the first waveguide bore 2526a and the path length P2 of the second waveguide bore 2526b differ by one-half wavelength so that the acoustic signals S1, S2 arrive at the emitting opening 2521 of the stylus housing 2520 in-phase with one another. Note that the first and second waveguide bores 2526a, 2526b are separate from one another so as to avoid mixing of the acoustic signals S1, S2 until they merge together at exit the stylus in the "in-phase" condition. Note further that the path lengths P1, P2 are defined by the propagative distance from the narrow gap apertures 2502$_F$, 2502$_B$ to the emitting opening 2521 of the stylus housing 2520.

FIG. 30 shows another embodiment of a handheld stylus 2600 similar to that shown in FIG. 28, comprising a pair of identically configured FUTs 2040$_1$, 2040$_2$ disposed opposite one another within the stylus housing 2620, and parallel with the longitudinal axis LA of the stylus housing 2620. Further, the stylus housing 2620 now includes apertures 2602$_{B1}$, 2602$_{B2}$ formed on back walls B$_{W1}$, B$_{W2}$ of back cavities B$_1$, B$_2$, respectively, for enabling acoustic signals S2 and S3 to propagate along respective waveguide bores 2626$_1$ and 2626$_2$. In this embodiment, the path lengths associated with each of the waveguide bores 2626$_1$ and 2626$_2$ differ from the path length of waveguide bore 2626 by an amount corresponding to one-half wavelength. The acoustic signals S1, S2 and S3 output at the emitting opening 2621 of the stylus housing 2620, thus, arrive in-phase and generate an increased-acoustic output signal corresponding to the aggregate amplitudes of each of the S1, S2 and S3 acoustic signals.

FIGS. 31A and 31B show partial views of two embodiments of a handheld stylus 2700, 2700' having multiple FUTs 2040$_1$, 2040$_2$, 2040$_3$, 2040$_4$, . . . , disposed within a stylus housing 2720, 2720' and aligned toward the axial direction of the stylus 2700, 2700'. The embodiments differ in how the FUTs 2040$_1$, 2040$_2$, 2040$_3$, 2040$_4$, . . . , are driven with voltage phases to generate an acoustic signal S propagating along bore 2726, 2726'. As shown in FIGS. 31A and 31B the center-to-center distance D1 between adjacent FUTs (e.g. between 2040$_1$ and 2040$_2$, 2040$_3$, 2040$_4$, . . . ) is one-half wavelength of the propagation medium (e.g. air). In the embodiment of FIG. 31A, the FUTs 2040$_1$, 2040$_2$, 2040$_3$, 2040$_4$, . . . , are driven by an AC drive source 2772, using electrodes disposed on sides e$_1$ of the transducer materials 2042$_1$, 2042$_2$, 2042$_3$, 2042$_4$, . . . , which are commonly connected to positive terminal V$_1$, and electrodes disposed on sides e$_2$ of the transducer films 2042$_1$, 2042$_2$, 2042$_3$, 2042$_4$, . . . , which are commonly connected to ground terminal Vg. The polarization of the FUTs 2040$_1$, 2040$_2$, 2040$_3$, 2040$_4$, . . . , alternate in the opposite direction to enable constructive interference of the resultant acoustic signals propagating along waveguide bore 2726 when driven by common drive source 2772.

In the embodiment of FIG. 31B, the polarization directions of all the FUT elements 2040$_1$, 2040$_2$, 2040$_3$, 2040$_4$, . . . , are aligned to the same direction, but the connection is different to the electrodes, as every other FUT 2040$_1$, 2040$_3$, . . . , is commonly connected to one side of the drive source 2772' to provide constructive interference. In both embodiments of FIGS. 31A and 31B, the acoustic waves radiated from adjacent FUTs have a phase difference of 180 degrees due to the periodicity of one-half wavelength. This phase difference is canceled by the difference of vibration phase (i.e. opposite phase for each adjacent FUT) so that the radiated waves from all of the FUTs are effectively summed in-phase such that when N units of FUTs as shown in FIGS. 31A, 31B are used, the acoustic pressure increases by about a factor of N, compared with only one FUT.

FIG. 32A shows a partial view of another embodiment of a handheld stylus 2800 having multiple opposing pairs of FUTs 2040$_{A1}$, 2040$_{B1}$, 2040$_{A2}$, 2040$_{B2}$, . . . , disposed (within the stylus housing 2820) parallel with the longitudinal axis LA of the stylus housing 2820. The FUTs of each pair complement one another to provide an enhanced acoustic signal S1 down a common waveguide bore 2826. The FUTs 2040$_{A1}$, 2040$_{B1}$, 2040$_{A2}$, 2040$_{B2}$, . . . , are driven by drive source 2872 with each pair of FUTs 2040$_{A1}$, 2040$_{B1}$, . . . , having the same polarization, but with the electrodes of every other FUT 2040$_{A1}$, 2040$_{A3}$, . . . and 2040$_{B1}$, 2040$_{B3}$, . . . , on each axial path commonly connected to one side of the drive source 2872 analogous to the embodiment shown in FIG. 31B, to provide constructive interference of the propagating acoustic signal.

FIG. 32B shows yet another embodiment of a handheld stylus 2900 (with the connection to drive source not shown) that is similar to the embodiment shown in FIG. 29A but including multiple FUTs 2040$_1$, 2040$_2$, 2040$_3$, 2040$_4$, disposed (within the stylus housing 2920) parallel with the longitudinal axis LA of the stylus housing 2920 and transmitting acoustic signals S1, S2 down respective waveguide bores 2926$_1$, 2926$_2$ which exit at an emitting opening of the stylus housing 2920. Note that in the embodiments shown in FIGS. 31A–B and 32A–B, the drive circuit driven FUTs generate an acoustic signal that linearly increases with time (i.e. the acoustic signal output increases with increasing drive cycles). Alternatively, according to an additional aspect of the invention, each FUT may be driven by a driver having a time delay of drive voltage, corresponding to the propagation time of the acoustic signal output from a given FUT to the next adjacent FUT position along the waveguide bore or narrow gap, so that the phase relationship between the axially propagating acoustic wave from each FUT and the waveform of the drive voltage is the same for all FUTs. This enables the bandwidth of the stylus to be quite broad, while also enabling the amplitude of the excited acoustic wave to be, in effect, multiplied by each of the multiple FUTs axially aligned with and appropriately spaced apart from one another, thereby providing a very strong acoustic signal after only a few cycles.

FIG. 33 shows an embodiment of a sequential drive circuit 4000 having delay segments for delaying excitation of FUTs 2040$_1$, 2040$_2$, 2040$_3$, and 2040$_4$ in accordance with the distance between the FUTs 2040$_1$, 2040$_2$, 2040$_3$, and 2040$_4$ and the propagation speed within the medium. Note that the FUTs 2040$_1$, 2040$_2$, 2040$_3$, and 2040$_4$ may each be individual transmitters in axial alignment with one another, or may each be a complementary set disposed opposite one another as illustrated in FIG. 32A, for example. Note that in this sequential structure, the center to center distance d between axial adjacent FUTs need not be limited to one-half wavelength, but may be larger or smaller, with the delay time t of the drive voltage, compared with adjacent FUTs located on the upstream side given by t=d/Vs where Vs is the acoustic velocity in the medium (e.g. air, Vs=344 m/sec). FIG. 34 is a graphical illustration of the excitation of each of the FUTs 2040$_1$, 2040$_2$, 2040$_3$, and 2040$_4$ as a function of time by the sequential drive circuit of FIG. 33.

FIG. 35 illustrates another embodiment of a FUT according to the invention, denoted by numeral 2040'. In this embodiment, the FUT comprises a flat, elongated, rectangular diaphragm 2044' and a flat, elongated rectangular piezoelectric transducer material 2042', made, for example, of PZT material, adhesively bonded to the diaphragm 2044'. A plurality of spaced apart electrodes 2045A, 2045B, 2045C, and 2045D are disposed on one surface of the transducer material 2042' and common ground on the opposite surface, thereby forming a plurality of corresponding transducer segments. The electrodes 2045A, 2045B, 2045C, and 2045D are sequentially excited by sequential drive circuit 4000 with a time difference of the drive voltage for each electrode matching the vibration time delay of the corresponding transducer segment. That is the excited vibration at one transducer segment propagates along the longitude direction such that in the matching condition the propagating vibration is effectively amplified by the sequential drive unit 4000. When sequential electrodes are excited, the time difference of the drive voltage should match the vibration time delay. When the propagation velocity of vibration is $V_b$, the time lag between two adjacent transducer segments is $d/v_b$, and the two adjacent units are driven with the same time lag as $d/v_b$. When the propagation velocity of vibration matches the acoustic propagation velocity in the medium (e.g., air) at the surface of the FUT 2040' the acoustic wave is effectively excited and used as a radiation source from the emitting opening of the stylus housing. The frequency response for the drive voltage to the acoustic response is characterized by a very broad band, and the excited signal becomes very strong from an initial cycle. FIG. 36 is an exemplary illustration showing the acoustic propagation path associated with a sequentially driven multi electrode FUT 2040' shown in FIG. 35.

FIG. 37 shows yet another embodiment of a handheld stylus 3000 that utilizes acoustic output signals from the both the front and back sides of a circular FUT 2040" to provide an enhanced output signal at the emitting opening 3021 of the stylus housing 3020. As shown therein, FUT 2040" comprises a thin, flat circular diaphragm 2044" having a centrally located aperture 2044a", and a thin, flat, circular piezoelectric transducer material 2042" having a centrally located aperture 2042a". The transducer material 2042" is adhesively bonded to the diaphragm 2044" such that the apertures 2042a" and 2044a" are axially aligned with one another. Note that apertures 2042a" and 2044a" are parts of a cylindrical narrow gap. The FUT 2040" is disposed perpendicular to the longitudinal axis LA of the stylus housing 3020. The apertures 2042a", 2044a" are axially aligned with a central waveguide bore 3026c, a central aperture 3027a of a FUT blocking structure 3027, a central aperture 3045a of a FUT retaining plug 3045, and an emitting opening 3021 of the stylus housing 3020. A writing and drawing implement 3050 extends through FUT apertures 2042a", 2044a", central waveguide bore 3026c, blocking structure aperture 3027a, plug aperture 3045a, and stylus housing emitting opening 3021. Upon excitation of the FUT 2040", an acoustic signal SI outputted toward the FUT back side facing surface B of the FUT retaining plug 3045, is guided to the emitting opening 3021 through the central waveguide bore 3026c. Front acoustic signals S2, S3 output from the front side of the FUT 2040" toward the FUT front side facing surface F of the blocking structure 3027 propagate along outer waveguide bores 3026a, 3026b and are collected at the emitting opening 3021 of the stylus housing 3020 so that the phase of both signals S2, S3 are in phase with one another when emitted from the emitting opening 3021 of the stylus housing 3020. Note that blocking structure 3027 formed within the stylus housing neck portion 3024 serves to block the propagation and free motion of the FUT diaphragm 2044" so as to prevent acoustic pressure generated from the FUT's back side (the side facing the retaining plug 3045) from propagating through the waveguide bores 3026a, 3026b, thus, causing this pressure to propagate through the central waveguide bore 3026c to the emitting opening of the stylus housing 3021. The blocking structure 3027 similarly prevents propagation of the acoustic signals S3, S4 generated at the front side of the FUT 2040" (the side facing the blocking structure 3027) from propagating down central waveguide bore 3026c. Note further that the propagation path lengths defined by the FUT front side waveguide bores 3026a, 3026b and the FUT back side waveguide bore 3026c are different. This difference may be configured to be one-half wavelength which cancels the 180 degree phase difference between the front and the back propagating acoustic signals and enables constructive interference of the signals S1, S2, and S3.

A further aspect of the invention involves the use of the piezoelectric function of the FUT 2040 to detect a force. This aspect of the invention will be described with reference to FIG. 48, which shows an embodiment of a handheld stylus 3400 made according to this aspect of the invention. The stylus 3400 comprises a FUT 2040 mounted within an interior 3429 of a cylindrical portion 3422 of a stylus housing 3420, the FUT 2040 transmitting acoustic signals along a longitudinal axis LA of the stylus housing 3420, which are emitted from an emitting opening 3421 of the stylus housing 3420. A writing and drawing implement 3450, such as an ink cartridge, for example, is disposed within the interior 3429 of the housing 3429 and retained by holder 3454 (made of a deformable material) to detect a force applied to the tip of the implement 3450, in order to ascertain whether the stylus 3400 is in a pen-up or pen-down position. In accordance with this aspect of the invention, the piezoelectric function of the FUT 2040 is used for the force detection. That is, a user initiates writing by applying the writing and drawing implement 3450 to a surface, the force F applied to the implement tip causing longitudinal movement of the implement 3450 in the direction given by arrow A to cause the opposite end 3423 of the implement 3450 to be applied against the outer surface 2044o of the diaphragm 2044 so that the diaphragm 2044 is deflected inward (i.e. in the direction of arrow A). During the writing period, the diaphragm 2044 must vibrate to generate the acoustic signals output from the emitting opening 3421 of the stylus housing 3420. Thus, the contact end 3423 of the implement 3450 (which contacts the diaphragm 2044) comprises a soft elastic material such as silicone rubber, for example, so as not to suppress the vibration. The contact material has an additional advantageous function of damping the vibrations of the diaphragm 2044 to minimize the strong resonance and ringing of the FUT 2040. When a user stops writing, the force exerted by the user on the implement 3450 to engage the writing surface becomes zero, resulting in longitudinal movement of the implement 3450 in the direction opposite arrow A such that diaphragm contact end 3423 of the implement is again spaced apart from the outer surface 2044o of the diaphragm 2044. The inward deflection of the diaphragm 2044, thus, becomes zero. The piezoelectric transducer material 2042 bonded to inner surface 2044i of the diaphragm 2044 generates a voltage signal only at the beginning and end of the writing period, with the polarity of the voltage at the beginning being opposite that of the end of the writing, as shown in the exemplary illustration of FIG. 39. This is typical of a piezoelectric response when a resistor R is connected in parallel with the piezoelectric transducer film 2042.

The writing and drawing implement 3450 is retained by an elastic retainer structure 3454 which controls the position of the implement 3450 so as not to engage or touch the diaphragm 2044 of the FUT 2040 during a non-writing period. The retainer structure 3454 is preferably designed not to obstruct the wave propagation, therefore, the retainer structure 3454 should be a thin, flat resilient plate such as rubber disposed in parallel to the wave propagation.

FIG. 40 shows an exemplary circuit for switching the FUT 2040 "off" in the pen-up and switching the FUT 2040 "on" in the pen-down position. When the diaphragm 2044 is inwardly deflected during writing, a positive voltage is generated and a switch 5001 transitions to the "on" state with a dc voltage fed to a pulse oscillator 5002. When the deflection of the diaphragm 2044 becomes zero, a negative voltage is generated and the dc voltage feeding the pulse oscillator 5002 has to be shut off. The pulse oscillator 5002 drives the FUT 2040 during the period the implement tip of the stylus 3400 is touching the writing surface. Note that the terminal T1 in FIG. 40, is connected as shown in FIG. 38, to a resistor R through a capacitor C, which in turn is connected to the transducer film 2042.

As mentioned earlier, the ultrasonic transducer structures described herein and depicted in the Figures may also be utilized as a receiver, wherein an incident acoustic wave in the axial direction induces a voltage signal on the electrodes within the transducer indicative of the acoustic signal received.

While the foregoing invention has been described with reference to the above embodiments, various modifications and changes can be made without departing from the spirit of the invention. Accordingly, all such modifications and changes are considered to be within the scope of the appended claims.

What is claimed is:

1. An ultrasonic transducer comprising:
   a holder having at least two spaced apart cylindrical surfaces;
   a cylindrical piezoelectric film spanning between the at least two spaced apart cylindrical surfaces of the holder;
   an outer electrode segment disposed on an outer surface of the film; and
   an inner electrode segment disposed on an inner surface of the film;
   a cover spaced from the outer surface of the film, the cover including a flange restricting propagation of the radiating acoustic energy along a propagation path defined along an exterior of the film;
   wherein the transducer radiates acoustic energy substantially along a longitudinal axis thereof in response to an excitation voltage applied to the film via the electrode segments.

2. The transducer of claim 1, further comprising a reflector disposed at an end thereof for redirecting the radiating acoustic energy in an opposite direction.

3. An ultrasonic transducer comprising:
   a holder having at least two spaced apart cylindrical surfaces;
   a cylindrical piezoelectric film spanning between the at least two spaced apart cylindrical surfaces of the holder;
   an outer electrode segment disposed on an outer surface of the film;
   an inner electrode segment disposed on an inner surface of the film;
   a reflector disposed at an end thereof for redirecting the radiating acoustic energy in an opposite direction;
   wherein the transducer radiates acoustic energy substantially along a longitudinal axis thereof in response to an excitation voltage applied to the film via the electrode segments.

4. An ultrasonic transducer comprising:
   a holder having at least two spaced apart cylindrical surfaces;
   a cylindrical piezoelectric film spanning between the at least two spaced apart cylindrical surfaces of the holder;
   an outer electrode segment disposed on an outer surface of the film; and
   an inner electrode segment disposed on an inner surface of the film,
   wherein: the at least two spaced apart cylindrical surfaces comprising a plurality of spaced apart cylindrical surfaces;

the film spanning between at least two pairs of the plurality of spaced apart cylindrical surfaces of the holder;

the outer electrode segment comprising a plurality of outer electrode segments; and the inner electrode segment comprising a plurality of inner electrode segments; and wherein the transducer radiates acoustic energy substantially along a longitudinal axis thereof in response to an excitation voltage applied to the film via the electrode segments.

5. The transducer of claim 4, further comprising a cover spaced from the outer surface of the film, the cover including a flange restricting propagation of the radiating acoustic energy along a propagation path defined along an exterior of the film.

6. The transducer of claim 5, further comprising a reflector disposed at an end thereof for redirecting the radiating acoustic energy in an opposite direction.

7. The transducer of claim 6, further comprising a reflector disposed at an end thereof for redirecting the radiating acoustic energy in an opposite direction.

8. An ultrasonic transducer comprising:

a holder having at least two spaced apart cylindrical surfaces;

a cylindrical piezoelectric film spanning between the at least two spaced apart cylindrical surfaces of the holder;

an outer electrode segment disposed on an outer surface of the film;

an inner electrode segment disposed on an inner surface of the film;

wherein the transducer radiates acoustic energy substantially along a longitudinal axis thereof in response to an excitation voltage applied to the film via the electrode segments and wherein the excitation voltage has a frequency which has a wavelength in a propagation medium, and a width of each of the electrode segments is about half of the wavelength.

9. The transducer of claim 8, further comprising a drive circuit for sequentially applying the excitation voltage to the electrode segments of the transducer.

10. An ultrasonic transducer comprising:

a holder having at least two spaced apart cylindrical surfaces;

a cylindrical piezoelectric film spanning between the at least two spaced apart cylindrical surfaces of the holder;

an outer electrode segment disposed on an outer surface of the film;

an inner electrode segment disposed on an inner surface of the film;

a drive circuit for sequentially applying an excitation voltage to the electrode segments of the transducer; and wherein the transducer radiates acoustic energy substantially along a longitudinal axis thereof in response to the excitation voltage applied to the film via the electrode segments.

11. The transducer of claim 4, wherein the excitation voltage has a frequency which has a wavelength in a propagation medium, wherein about half of the wavelength is more than a width of each of the electrode segments.

12. The transducer of claim 11, further comprising a drive circuit for sequentially applying the excitation voltage to the electrode segments of the transducer.

13. The transducer of claim 4, further comprising a drive circuit for sequentially applying the excitation voltage to the electrode segments of the transducer.

14. The transducer of claim 4, wherein the holder restricts propagation of the radiating acoustic energy along a propagation path defined within an interior of the film.

15. The transducer according to claim 4, wherein the electrode segments have a center to center distance of one-half of a wavelength and the electrode segments are driven such that every other one is driven in-phase with every adjacent electrode segment in opposite phase drive.

16. An ultrasonic transducer comprising:

a holder having at least two spaced apart cylindrical surfaces;

a cylindrical piezoelectric film spanning between the at least two spaced apart cylindrical surfaces of the holder;

an outer electrode segment disposed on an outer surface of the film; and an inner electrode segment disposed on an inner surface of the film;

wherein the transducer radiates acoustic energy substantially along a longitudinal axis thereof in response to an excitation voltage applied to the film via the electrode segments and wherein the excitation voltage has a frequency which has a wavelength in a propagation medium, and a width of each of the electrode segments is about 10 to 20 percent greater that one-half the wavelength.

* * * * *